(12) United States Patent
Shelton, IV et al.

(10) Patent No.: US 10,912,567 B2
(45) Date of Patent: Feb. 9, 2021

(54) CIRCULAR STAPLER

(71) Applicant: Ethicon LLC, Guaynabo, PR (US)

(72) Inventors: Frederick E. Shelton, IV, Hillsboro, OH (US); Jason L. Harris, Lebanon, OH (US); Chester O. Baxter, III, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 186 days.

(21) Appl. No.: 15/689,057

(22) Filed: Aug. 29, 2017

(65) Prior Publication Data
US 2019/0059900 A1 Feb. 28, 2019

(51) Int. Cl.
*A61B 17/115* (2006.01)
*A61B 17/11* (2006.01)
(Continued)

(52) U.S. Cl.
CPC ........... *A61B 17/1155* (2013.01); *A61B 17/32* (2013.01); *A61B 34/30* (2016.02); *A61B 2017/00017* (2013.01); *A61B 2017/00022* (2013.01); *A61B 2017/00212* (2013.01); *A61B 2017/00221* (2013.01); *A61B 2017/00398* (2013.01); *A61B 2017/00473* (2013.01); *A61B 2017/00477* (2013.01); *A61B 2017/00734* (2013.01); *A61B 2017/07242* (2013.01); *A61B 2017/07278* (2013.01); *A61B 2017/1132* (2013.01); *A61B 2090/061* (2016.02); *A61B 2090/062* (2016.02); *A61B 2090/066* (2016.02)

(58) Field of Classification Search
None
See application file for complete search history.

(56) References Cited

U.S. PATENT DOCUMENTS

| 5,322,055 A | 6/1994 | Davison et al. |
| 5,558,671 A | 9/1996 | Yates |

(Continued)

FOREIGN PATENT DOCUMENTS

| EP | 3078335 A1 | 10/2016 |
| WO | 2014151621 A1 | 9/2014 |
| WO | 2014151952 A1 | 9/2014 |

OTHER PUBLICATIONS

U.S. Appl. No. 15/200,283 entitled "Methods, Systems, and Devices for Initializing a Surgical Tool" filed Jul. 1, 2016.

(Continued)

*Primary Examiner* — Martin T Ton
(74) *Attorney, Agent, or Firm* — Mintz Levin Cohn Ferris Glovsky and Popeo, P.C.

(57) ABSTRACT

Systems and methods for stapling tissue, a vessel, duct, etc., during a surgical procedure are provided. The surgical stapling systems generally include a circular stapling tool with a shaft extending therefrom that has an end effector at a distal end thereof. The end effector can have a staple deck and an anvil. The circular stapling tool can be configured to drive at least two circular rows of staples through tissue engaged between the staple deck and the anvil to thereby staple the tissue, and the tool can be configured to drive a knife through tissue engaged between the staple deck and the anvil to thereby cut the tissue. The surgical stapling system can also include a control system that is configured to communicate with the circular stapling tool.

20 Claims, 11 Drawing Sheets

(51) Int. Cl.
*A61B 17/00* (2006.01)
*A61B 17/32* (2006.01)
*A61B 90/00* (2016.01)
*A61B 34/30* (2016.01)
*A61B 17/072* (2006.01)

(56) References Cited

U.S. PATENT DOCUMENTS

| | | |
|---|---|---|
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,066,137 A | 5/2000 | Greep |
| 6,132,368 A | 10/2000 | Cooper |
| 6,168,605 B1 | 1/2001 | Measamer et al. |
| 6,179,195 B1 * | 1/2001 | Adams ............ A61B 17/07207 227/179.1 |
| 6,231,565 B1 | 5/2001 | Tovey et al. |
| 6,325,811 B1 | 12/2001 | Messerly |
| 6,364,888 B1 | 4/2002 | Niemeyer et al. |
| 6,500,176 B1 | 12/2002 | Truckai et al. |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckal et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 | 6/2013 | Holcomb et al. |
| 8,590,763 B2 | 11/2013 | Milliman |
| 8,602,286 B2 | 12/2013 | Crainich et al. |
| 8,602,287 B2 * | 12/2013 | Yates ............... A61B 17/07207 227/175.1 |
| 8,684,253 B2 | 4/2014 | Giordano et al. |
| 8,771,270 B2 | 7/2014 | Burbank |
| 8,801,735 B2 | 8/2014 | Shelton, IV et al. |
| 8,986,302 B2 | 3/2015 | Aldridge et al. |
| 9,023,071 B2 | 5/2015 | Miller et al. |
| 9,072,536 B2 | 7/2015 | Shelton, IV et al. |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,393,037 B2 | 7/2016 | Olson et al. |
| 9,445,816 B2 | 9/2016 | Swayze et al. |
| 9,554,802 B2 | 1/2017 | Williams et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 2002/0185517 A1 * | 12/2002 | Vresh ................ A61B 17/1114 227/176.1 |
| 2006/0079874 A1 | 4/2006 | Faller et al. |
| 2006/0097025 A1 | 5/2006 | Milliman et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0038401 A1 | 2/2010 | Milliman et al. |
| 2010/0191282 A1 | 7/2010 | Harris et al. |
| 2010/0198248 A1 | 8/2010 | Vakharia |
| 2011/0015631 A1 | 1/2011 | Wiener et al. |
| 2011/0087218 A1 | 4/2011 | Boudreaux et al. |
| 2011/0087256 A1 | 4/2011 | Wiener et al. |
| 2011/0295270 A1 | 12/2011 | Giordano et al. |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0292367 A1 | 11/2012 | Morgan et al. |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0261648 A1 | 10/2013 | Laurent et al. |
| 2013/0325034 A1 | 12/2013 | Schena et al. |
| 2014/0005718 A1 | 1/2014 | Shelton, IV et al. |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0246476 A1 * | 9/2014 | Hall ..................... A61B 17/068 227/175.1 |
| 2014/0252062 A1 | 9/2014 | Mozdzierz |
| 2014/0263539 A1 * | 9/2014 | Leimbach ........ A61B 17/07207 227/175.1 |
| 2014/0263541 A1 | 9/2014 | Leimbach et al. |
| 2014/0276931 A1 | 9/2014 | Parihar et al. |
| 2015/0209059 A1 | 7/2015 | Trees et al. |
| 2015/0209573 A1 | 7/2015 | Hibner et al. |
| 2015/0272575 A1 | 10/2015 | Leimbach et al. |
| 2015/0282825 A1 | 10/2015 | Trees et al. |
| 2015/0305742 A1 | 10/2015 | Williams |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089533 A1 | 3/2016 | Turner et al. |
| 2016/0157855 A1 | 6/2016 | Williams |
| 2016/0175060 A1 | 6/2016 | Park |
| 2016/0287252 A1 | 10/2016 | Parihar |
| 2016/0317152 A1 | 11/2016 | Scirica et al. |
| 2016/0367243 A1 | 12/2016 | Martin et al. |
| 2017/0000486 A1 | 1/2017 | Penna et al. |
| 2017/0056038 A1 | 3/2017 | Hess et al. |
| 2017/0196637 A1 | 7/2017 | Shelton, IV et al. |
| 2017/0202609 A1 | 7/2017 | Shelton, IV et al. |
| 2018/0353185 A1 | 12/2018 | Nicholas |
| 2018/0360459 A1 * | 12/2018 | Bilotti ................ A61B 17/1155 |
| 2019/0059884 A1 | 2/2019 | Shelton, IV et al. |

OTHER PUBLICATIONS

U.S. Appl. No. 15/237,653 entitled "Methods, Systems, and Devices for Controlling a Motor of a Robotio Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

U.S. Appl. No. 15/674,075 entitled "Clip Retention for Surgical Clip Applier" filed Aug. 10, 2017.

U.S. Appl. No. 15/674,086 entitled "Surgical Clip Applier Jaw Alignment" filed Aug. 10, 2017.

U.S. Appl. No. 15/674,096 entitled "Surgical Device with Overload Mechanism" filed Aug. 10, 2017.

U.S. Appl. No. 15/674,121 entitled "Jaw for Clip Applier" filed Aug. 10, 2017.

U.S. Appl. No. 15/674,125 entitled "Clip Appliers with Extended Jaw Tip" filed Aug. 10, 2017.

U.S. Appl. No. 15/674,166 entitled "Surgical Clip Applier" filed Aug. 10, 2017.

U.S. Appl. No. 15/689,072 entitled "Methods, Systems, and Devices for Controlling Electrosurgical Tools" filed Aug. 29, 2017.

(56) References Cited

OTHER PUBLICATIONS

U.S. Appl. No. 29/613,511 entitled "Clip Applier Rotation Knob" filed Aug. 10, 2017.
International Preliminary Report on Patentability received for PCT International Application No. PCT11B20181056330, dated Mar. 12, 2020, 13 pages.
International Search Report received for PCT Patent International Application No. PCT/1132018/056330, dated Jan. 8, 2019, 22 pages.
U.S. Appl. No. 15/689,060, filed Aug. 29, 2017, Circular Stapler.

* cited by examiner

CIRCULAR STAPLER

FIELD

Electrically-powered surgical staplers and methods for using the same are provided.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices can be less precise in operation than manually-operated devices. For example, users of manually-operated devices are able to instantly stop the progress of a mechanism by simply releasing the actuation mechanism. With an electrically-powered device, however, releasing an actuation button or switch may not result in instantaneous halting of a mechanism, as the electric motor may continue to drive the mechanism until the kinetic energy of its moving components is dissipated. As a result, a mechanism may continue to advance for some amount of time even after a user releases an actuation button.

Accordingly, there remains a need for improved devices and methods that address current issues with electrically-powered surgical devices.

SUMMARY

Surgical stapling systems and methods for using the same are provided herein.

In one exemplary embodiment, a surgical stapling system is provided that includes a circular stapling tool with a housing and an instrument shaft extending therefrom with an end effector at a distal end thereof. The end effector can include a staple deck and an anvil movable relative to the staple deck. The circular stapling tool can be configured to drive inner and outer circular rows of staples through tissue engaged between the staple deck and the anvil to thereby staple the tissue. The circular stapling tool can also be configured to drive a knife through tissue engaged between the staple deck and the anvil to thereby cut the tissue. The system can also include a control system that is configured to communicate with the circular stapling tool and that is configured to selectively actuate the circular stapling tool to independently drive any one of the inner circular row of staples, the outer circular row of staples, and the knife.

The system can have numerous variations. For example, the control system can be configured to initiate actuation of the knife prior to commencement of actuation of at least one of the inner circular row of staples and the outer circular row of staples. In some examples, the circular stapling tool can include an inner staple drive assembly operable to drive the inner circular row of staples through the staple deck toward the anvil, an outer staple drive assembly operable to drive the outer circular row of staples through the staple deck toward the anvil, and a knife drive assembly configured to drive the knife through the staple deck toward the anvil.

The housing can be configured as a hand-held device, or in other embodiments the housing can include a tool mounting portion configured to mount to a motor housing on a surgical robot.

In one embodiment, the control system can be configured to control a displacement of the anvil from the staple deck and drive the knife when a threshold displacement is reached. In another example, the control system can be configured to monitor a displacement of the knife from the housing and retract the knife when the knife reaches a threshold displacement away from the housing. The control system can also be configured to drive any one of the inner circular row of staples, the outer circular row of staples, and the knife based on a predetermined time offset after driving one of the others of the inner circular row of staples, the outer circular row of staples, and the knife.

In another embodiment, the control system can be configured to control a travel distance of the inner staple drive assembly and the outer staple drive assembly. The control system can also be configured to control a rate of advancement of at least one of the inner staple drive assembly, the outer staple drive assembly, and the knife drive assembly based on a measured thickness of a tissue engaged between the anvil and the staple deck.

In another exemplary embodiment, a surgical stapling system is provided that includes an electromechanical tool with an instrument shaft and an end effector at a distal end thereof. The end effector can include a staple deck having inner and outer rows of staples disposed therein and an anvil movable relative to the staple deck. An inner staple driver can be operable to drive the inner row of staples through the staple deck toward the anvil. The end effector can also have an outer staple driver operable to drive the outer row of staples through the staple deck toward the anvil and a knife that is movable through an opening in the staple deck for cutting tissue engaged between the staple deck and the anvil. The system can also include a housing coupled to the shaft that has drive assemblies. The drive assemblies include an inner staple drive assembly operable to drive the inner stapler driver, an outer staple drive assembly operable to drive the outer staple driver, and a knife drive assembly operable to drive the knife. The system can further include a control system that is configured to communicate with the electromechanical tool and that is configured to selectively initiate actuation of each of the drive assemblies. This actuation can cause any one of the inner staple drive assembly, the outer staple drive assembly, and the knife drive assembly to be actuated prior to commencement of actuation of any other one of the inner staple drive assembly, the outer staple drive assembly, and the knife drive assembly.

The system can have various embodiments. For example, the control system can be configured to control a travel distance of the inner staple drive assembly and the outer staple drive assembly to thereby control a shape of staples being formed by the anvil. The control system can also be configured to control a rate of advancement of at least one of the inner staple drive assembly, the outer staple drive assembly, and the knife drive assembly based on a measured thickness of a tissue engaged between the anvil and the staple deck.

The housing can be configured as a hand-held device, such as with a battery disposed within the housing. In other embodiments, the housing can include a tool mounting portion configured to mount to a motor housing on a surgical robot.

In another aspect, a method for stapling tissue is provided that includes manipulating a surgical stapling device to engage tissue between an anvil and a staple deck on an end effector of the surgical stapling device. The method can also include inputting a command into a control system to instruct the control system to initiate actuation of the surgical stapling device. The control system can communicate with the surgical stapling device to independently actuate each of an inner staple drive assembly to drive an inner circular row of staples from the staple deck toward the anvil to staple the tissue engaged therebetween, an outer staple drive assembly to drive an outer circular row of staples from the staple deck toward the anvil to staple the tissue engaged therebetween, and a knife drive assembly to drive a knife from the staple deck toward the anvil to cut the tissue engaged therebetween.

The method can have numerous variations. In one example, the control system can wirelessly communicate with the surgical stapling device to actuate the surgical stapling device. In another example, the control system can control a travel distance of the inner staple drive assembly and the outer staple drive assembly to thereby control a shape of staples being formed by the anvil. The travel distance can be controlled based on a measured thickness of the tissue engaged between the staple deck and the anvil. In one example, the control system can control a rate of advancement of at least one of the inner staple drive assembly, the outer staple drive assembly, and the knife drive assembly based on a measured thickness of the tissue engaged between the staple deck and the anvil. In another example, manipulating a surgical stapling device can include manipulating a user input device wirelessly coupled to a surgical robotic system having the surgical stapling device coupled thereto. Manipulating a surgical stapling device can also include manipulating a handle housing of the surgical stapling device.

In another aspect, a surgical stapling system is provided that includes a circular stapling tool with a housing and an instrument shaft extending therefrom with an end effector at a distal end thereof. The end effector can include a staple deck and an anvil movable relative to the staple deck. The circular stapling tool can have a staple drive assembly that is configured to drive inner and outer circular rows of staples through tissue engaged between the staple deck and the anvil to thereby staple the tissue and can also have a knife drive assembly that is configured to drive a knife through tissue engaged between the staple deck and the anvil to thereby cut the tissue. The system can also include a control system that is configured to control advancement of the knife drive assembly toward the anvil and is configured to stop advancement of the knife drive assembly when the control system detects that the knife has fully passed through tissue engaged between the staple deck and the anvil.

The system can have a variety of embodiments. For example, the control system can detect that the knife has fully passed through tissue by monitoring a force required to advance the knife drive assembly. In another example, when the force required to advance the knife drive assembly changes at a rate that exceeds a predetermined threshold rate of change, the control system can stop advancement of the knife drive assembly. In another example, when the force required to advance the knife drive assembly changes by an amount that exceeds a predetermined delta, the control system can stop advancement of the knife drive assembly. The knife drive assembly can be coupled to a motor that advances the knife drive assembly, and the force to advance the knife drive assembly can be measured based on a current required to drive the motor.

In some embodiments, the control system can detect that the knife has fully passed through tissue by monitoring a velocity of the knife drive assembly. In another example, when the velocity of the knife drive assembly changes by an amount that exceeds a predetermined delta, the control system can stop advancement of the knife drive assembly. In one example, the control system can stop advancement of the knife drive assembly when the knife contacts a knife support surface on the anvil.

The housing of the device can be configured as a hand-held tool, or in other embodiments the housing can include a tool mounting portion that is configured to mount to a motor housing on a surgical robot when the control system is coupled to the surgical robot. The housing can include at least one motor disposed therein for driving the staple drive assembly and the knife drive assembly and at least one actuator thereon for actuating the at least one motor.

In another embodiment, a surgical stapling system is provided with an electromechanical tool that includes an instrument shaft and an end effector at a distal end thereof. The end effector can include a staple deck with inner and outer rows of staples disposed therein and an anvil movable relative to the staple deck. The end effector can also include an inner staple driver operable to drive the inner row of staples through the staple deck toward the anvil, an outer staple driver operable to drive the outer row of staples through the staple deck toward the anvil, and a knife that is movable through an opening in the staple deck for cutting tissue engaged between the staple deck and the anvil. The system can include a housing coupled to the shaft. The housing can have drive assemblies that include at least one staple drive assembly operable to drive the inner and outer staple drivers and a knife drive assembly operable to drive the knife. The system can also include a control system that is configured to communicate with the electromechanical tool and configured to actuate and control the drive assemblies. The control system can be configured to control the knife drive assembly based on at least one of a force required to advance the knife drive assembly and a velocity of the knife drive assembly.

The system can vary in numerous ways. For example, the at least one staple drive assembly can include an inner staple drive assembly operable to drive the inner staple drivers and an outer drive assembly operable to drive the outer staple drivers. In another example, the control system can be configured to detect passage of the knife through tissue engaged between the staple deck and the anvil based on at least one of the force and the velocity. The control system can be configured to stop advancement of the knife drive assembly when the control system detects passage of the knife through tissue engaged between the staple deck and the anvil based on at least one of the force and the velocity. In one example, when the force required to advance the knife drive assembly changes at a rate that exceeds a predetermined threshold rate of change, the control system can stop advancement of the knife drive assembly. In another example, when the force required to advance the knife drive assembly changes by an amount that exceeds a predetermined delta, the control system can stop advancement of the knife drive assembly.

In another example, the knife drive assembly can be coupled to a motor that advances the knife drive assembly, and the force to advance the knife drive assembly can be measured based on a current required to drive the motor. In one embodiment, when the velocity of the knife drive assembly changes by an amount that exceeds a predetermined delta, the control system can stop advancement of the knife drive assembly. In another example, the control system can be configured to stop advancement of the knife drive assembly when the knife contacts a knife support surface on the anvil. The housing can also include a tool mounting portion that is configured to mount to a motor housing on a surgical robot, and the control system can be coupled to the surgical robot. The housing can include at least one motor disposed therein for driving the staple drive assembly and the knife drive assembly, and at least one actuator thereon for actuating the at least one motor.

In another aspect, a method for stapling tissue is provided that includes manipulating a surgical stapling device to engage tissue between an anvil and a staple deck on an end effector of the surgical stapling device. The method can also include inputting a command into a control system such that the control system initiates actuation of the surgical stapling device. The control system can communicate with the surgical stapling device to advance the knife drive assembly to drive a knife from the staple deck toward the anvil to cut the tissue engaged therebetween, and to stop advancement of the knife drive assembly when the control system detects that the knife has fully passed through the tissue.

The method can have numerous variations. For example, the control system can detect that the knife has fully passed through the tissue by monitoring a force required to advance the knife drive assembly. The control system can also detect that the knife has fully passed through the tissue by monitoring a velocity of the knife drive assembly. In another example, the control system can wirelessly communicate with the surgical stapling device to actuate the surgical stapling device. Manipulating a surgical stapling device can include manipulating a user input device wirelessly coupled to a surgical robotic system having the surgical stapling device coupled thereto. In another example, manipulating a surgical stapling device can include manipulating a handle housing of the surgical stapling device.

BRIEF DESCRIPTION OF DRAWINGS

This invention will be more fully understood from the following detailed description taken in conjunction with the accompanying drawings, in which.

DETAILED DESCRIPTION

Figure 1:
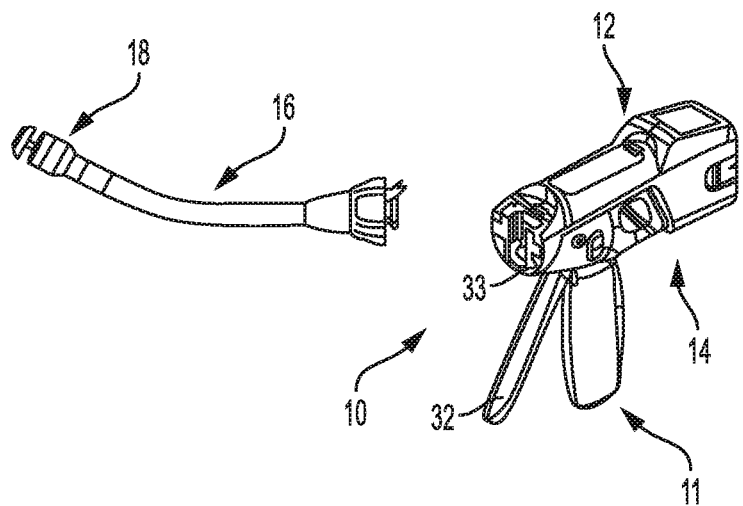
FIG. 1 is a side perspective view of one exemplary embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Circular staplers can be used in a variety of surgical procedures (e.g., colorectal, bariatric, thoracic, etc.) to clamp down on layers of tissue, drive staples through clamped layers of tissue, and cut through clamped layers of tissue to substantially seal layers of tissue together near the severed ends of the tissue layers, thereby joining severed ends and creating an anatomical lumen. In some instances, when using a circular stapler to form an end-to-end anastomosis, staple formation and anastomosis integrity may be inadvertently and negatively affected by, for example, initially driving an annular row of staples through tissue while simultaneously severing excess tissue. For instance, when an initial row of staples is formed simultaneously during excess tissue severing, stapled tissue may begin to move due to forces absorbed from severing of excess tissue before staples are fully formed. Movement of stapled tissue before full formation of an initial row of staples may adversely impact the quality of an end-to-end anastomosis. Therefore, it may be desirable to fire a first row of staples into tissue before severing excess tissue. Firing a first row of staples into tissue before severing tissue may prevent unwanted movement of stapled tissue before completion of staple formation, which may increase the integrity of staple formation in an end-to-end anastomosis. Additionally, staple formation may be negatively affected by simultaneously driving multiple annular staple rows to form an end-to-end anastomosis. Therefore, it may also be desirable to fire a first annular row of staples into tissue, and then fire an additional annular row(s) of staples into tissue sequentially before severing excess tissue. Alternatively, it may be desirable to fire a first annular row of staples into tissue before severing excess tissue, and then fire a second annular row of staples into tissue while simultaneously severing excess tissue. Firing a first row of staples into tissue may allow for the general shape of an end-to-end anastomosis for form, while sequentially firing a second row of staples into tissue may allow for a finer cinching of the end-to-end anastomosis to develop. It is therefore desirable to have a circular stapler with capabilities of independently firing annular rows of staples, and/or independently firing a knife assembly to sever excess tissue.

Accordingly, systems and methods for stapling tissue, a vessel, duct, etc., during a surgical procedure are provided. The systems and methods can be used in connection with a circular stapling tool having a housing with a shaft extending therefrom that has an end effector at a distal end thereof. The end effector can have a staple deck and an anvil. The circular stapling tool can be configured to drive at least two circular rows of staples through tissue engaged between the staple deck and the anvil to thereby staple the tissue, and the tool can be configured to drive a knife through tissue engaged between the staple deck and the anvil to thereby cut the tissue. A control system is provided that can be configured to communicate with a circular stapling tool and that is configured to selectively actuate the circular stapling tool to independently drive any one of the individual circular rows of staples and the knife. The system can thus selectively actuate any one row of staples and/or the knife to allow the system to have a greater degree of control over when stapling and cutting occurs in tissue, giving a great deal more control and reliability to the system than in stapler versions that require simultaneous and/or overlapping stapling and cutting. In other embodiments, a control system can be configured to control advancement of the knife drive assembly toward the anvil and to stop advancement of the knife drive assembly when the control system detects that the knife has fully passed through the tissue. Because the system can stop advancement when the knife has fully passed through tissue, the system can provide more control to an operation while using less force on the knife and still ensuring tissue will be fully cut.

An exemplary surgical stapling system can include a variety of features to facilitate application of a surgical staple as described herein and illustrated in the drawings.

However, a person skilled in the art will appreciate that the surgical stapling systems can include only some of these features and/or it can include a variety of other features known in the art. The surgical stapling systems described herein are merely intended to represent certain exemplary embodiments. Moreover, while the drive and control systems are shown and described in connection with circular staplers, a person skilled in the art will appreciate that these systems can be used in connection with other surgical staples or surgical devices, such as forceps/graspers, needle drivers, scissors, electrocautery tools, clip appliers/removers, suction tools, irrigation tools, etc. Further, a person skilled in the art will appreciate that the surgical stapling systems described herein have application in conventional minimally-invasive and open surgical instrumentation as well as application in robotic-assisted surgery.

Surgical Stapling Device

As indicated above, in an exemplary embodiment control systems are provided for controlling actuation of a surgical stapling device. FIG. 1 illustrates one embodiment of a circular surgical stapler 10 for use with a control system. As shown in FIG. 1, the stapler 10 includes a handle assembly 11 and a removable shaft assembly 16. The illustrated handle assembly 11 includes a housing 12 with a stationary handle 14, a closure trigger 32, and a firing trigger 33. The housing 12 can be configured for operative attachment to a shaft assembly 16, which has a surgical end effector 18 at a distal end thereof. As illustrated, the shaft assembly 16 is releasable and removable from the housing 12, however the shaft assembly 16 can be integrally formed or fixedly attached to the housing. As described below, the end effector 18 is configured to perform one or more surgical tasks or procedures. In particular, end effector 18 shown in FIG. 1 is operable to perform a circular cutting and stapling procedure. The handle 14 operatively supports a drive system therein that is configured to generate and apply various control motions to corresponding drive assemblies extending through the shaft assembly 16. The drive system in the handle assembly 11 can include one or more gear assemblies that can be driven by one or more motors (not shown), either located in the handle assembly 11 or external to the handle assembly 11, e.g., within a surgical robotic system. In the illustrated hand-held embodiment, the motor(s) are located within the handle and powered by a battery. In certain exemplary embodiments, the drive assemblies can include a closure drive assembly that can function to close the anvil and grasp tissue by the end effector 18, one or more firing assemblies that can fire one or more staple rows disposed in the end effector 18 into tissue grasped by the end effector 18, and a cutting assembly that can fire a knife disposed in the end effector 18 to sever tissue grasped by the end effector 18.

Additional details regarding the drive system and various drive assemblies and the structure of the circular stapler are disclosed in U.S. patent application Ser. No. 15/634,620, filed Jun. 27, 2017, titled "Surgical Stapler with Independently Actuated Drivers to Provide Varying Staple Heights," which is incorporated herein by reference in its entirety. Additional details regarding the various circuitry and control systems used to actuate the circular stapler may be found in U.S. Pub. No. 2014/0263541, the disclosure of which is incorporated by reference herein and/or U.S. Pub. No. 2015/0272575, the disclosure of which is incorporated by reference herein. Additional details on surgical staplers, such as conventional surgical staplers, are disclosed in U.S. Pat. Nos. 8,469,252, 8,602,286 and 9,713,468, each of which is incorporated herein by reference in its entirety.

As previously noted, more and more surgical procedures are being performed using electrically-powered surgical devices that are either hand-held or that are coupled to a surgical robotic system. Unlike manually-operated devices, electrically-powered surgical devices can lack control and tactile feedback, thereby reducing a surgeon's ability to effectively, accurately, and safely use these devices. Further, manually-operated devices are typically displacement controlled in which mechanical hard stops are used to allow the device to shift to different stages of operation, for example, from firing to cutting. However, using mechanical stops has its disadvantages. For example, a user can be limited in assessing whether a jam has occurred in the device, if the staples are fully formed, or whether the knife has cut through the tissue.

Figure 2:
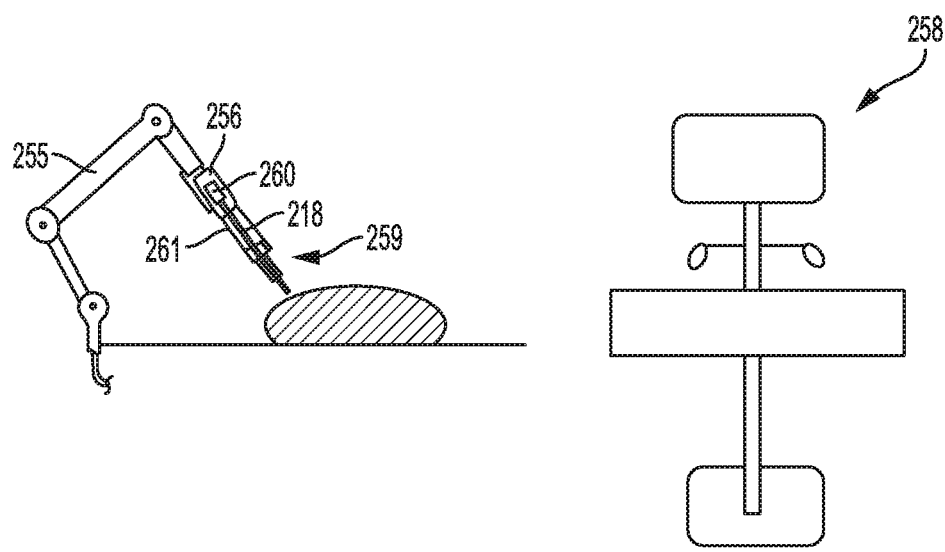
FIG. 2 is a side view of an exemplary embodiment of a surgical robotic system that includes a robotic arm having a drive system mounted in a motor housing on an end of the robotic arm, and that is wirelessly coupled to a control system.
Figure 3:
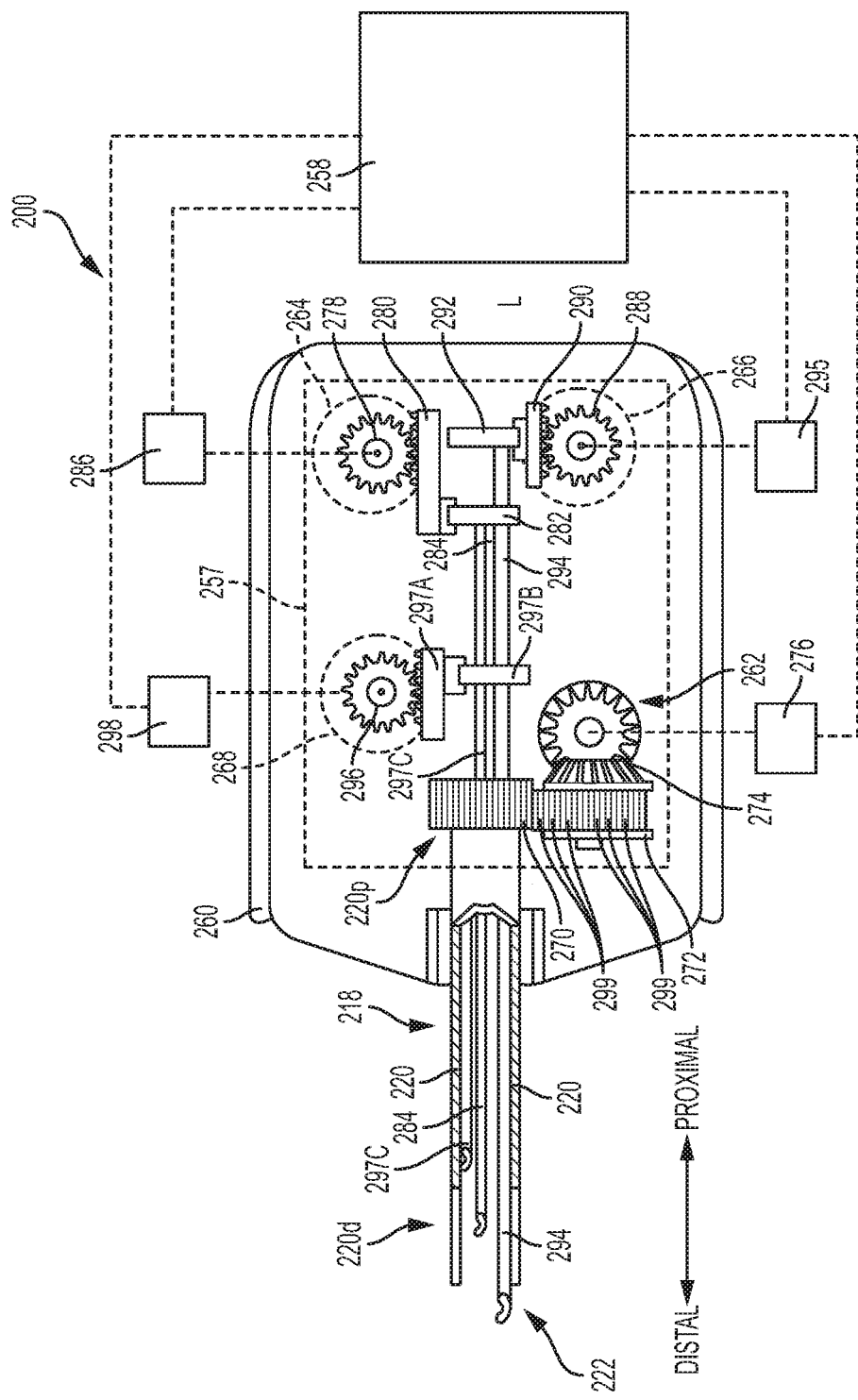
FIG. 3 is a side, partially transparent schematic view of an exemplary surgical stapling system having a staple shaft assembly that is coupled to a drive system, the drive system being coupled to motors that are operably coupled to a control system.

Accordingly various embodiments of drive and control systems are provided for producing real-time feedback during the operation of electrically-powered surgical devices so as to enable a surgeon or other user to effectively and accurately use such devices. In general, a drive system can be operably coupled to the staple shaft assembly and to at least one motor that is configured to drive various drive assemblies for actuating the device, and the control system can be operably coupled to the at least one motor and it can be configured to actuate the at least motor to drive the drive system and thereby control actuation of the drive assemblies. The control system and the motors can be disposed within the handle housing for use as a hand-held device, similar to the device of FIG. 1, or they can be located external to the handle housing, such as in a surgical robotic system. For example, FIG. 2 illustrates an exemplary embodiment of a surgical robotic system having a robotic arm 255 wirelessly coupled to a control system 258 with a console with a display and two user input devices. One or more motors (not shown) are disposed within a motor housing 256 that is coupled to an end of the robotic arm 255. A tool or drive system housing 260 on a surgical tool can house a drive system (not shown) and it can be mounted to the motor housing 256 to thereby operably couple the motor(s) to the drive system. As a result, when the motors are activated by the control system, the motor(s) can actuate the drive system, which in turn can drive the various drive assemblies. As shown in FIG. 3, a staple shaft assembly 218 extends from the tool housing 260. During surgery, the staple shaft assembly 218 can be placed within and extend through a trocar 259 that is mounted on the bottom of a carrier 261 extending between the motor housing 256 and a trocar support. The carrier 261 allows the tool to be translated into and out of the trocar 259.

Drive System

FIG. 3 illustrates an exemplary embodiment of surgical stapling system 200 having a tool housing 260 containing a drive system 257 and being coupled to a proximal end 220$p$ of an instrument shaft 220 of a staple shaft assembly 218. The drive system 257 is shown coupled to four motors 276, 286, 295, 298 that are operably coupled to a control system 258. As noted above, the motors and the control system can be located within the tool housing 260 to form a powered hand-held device, such as shown in FIG. 1, or they can be located external of the housing 260, such as in a robotic system as described with respect to FIG. 2. Moreover, aside from the differences described in detail below, the staple shaft assembly 218 can be similar to staple shaft assembly 18 of FIG. 1. Further, for purposes of simplicity, certain components of the staple shaft assembly 218 are not illustrated in FIG. 3.

While the drive system 257 can have a variety of configurations, in this exemplary embodiment, the drive system 257 includes gearing assemblies that are part of four drive assemblies: an anvil clamping drive assembly 262 configured to cause an anvil 600 to advance and retract in distal and proximal directions relative to the housing 260; an outer staple drive assembly 268 configured to cause an outer staple driver 750 to advance in distal and proximal directions relative to the housing 260 to deploy staples; an inner staple drive assembly 264 configured to cause an inner stapler driver 770 to advance in distal and proximal directions relative to the housing 260 to deploy staples; and a knife drive assembly 266 configured to cause a knife assembly 710 to advance in distal and proximal directions relative to the housing 260 to sever tissue. Additionally and/or alternatively, a shaft rotation mechanism can be incorporated into one or more of the drive assemblies to cause rotation of the instrument shaft 220. Each drive assembly, as well as the gearing in the drive system for driving the drive assemblies, is discussed in more detail below. Each gearing assembly in the drive system can be coupled to a rotary motor shaft of a corresponding motor. During actuation, the corresponding motor can actuate the gearing to thereby actuate the drive assemblies. Further, as described below, one or more motors can be coupled to a corresponding rotary encoder that provides displacement information to the control system 258 for at least one of the anvil clamping drive assembly 262, the outer staple drive assembly 268, the inner staple drive assembly 264, and the knife drive assembly 266 during operation of the drive system 257. Alternatively or in addition, the one or more motors can be coupled to a corresponding torque sensor that provides the control system 258 with information about the amount of force being applied to the motor(s) during operation of the drive system 257.

Motors

As noted above, one or more motors can be coupled to one or more drive assemblies of the drive system to move the anvil, drive the inner and/or outer rows of staples, and drive the knife or cutting element. The motor(s) can be located within the surgical device itself or, in the alternative, coupled to the surgical device such as via a robotic surgical system. Each motor can include a rotary motor shaft that is configured to couple to the drive system of the surgical device so that the motor can actuate the drive system to cause a variety of movements and actions of the device.

It should be noted that any number of motors can be used for driving any one or more gear assemblies of the drive system on a surgical device. For example, one motor can be used to actuate two different gear assemblies for actuating different drive assemblies. Moreover, in certain embodiments, the drive system can include a shift assembly for shifting the drive system between different modes for causing different actions. A single motor can in other aspects be coupled to a single drive assembly. A surgical device can include any number of drive assemblies and any number of motors for actuating the various drive assemblies. The motor(s) can be powered using various techniques, such as by a battery on the device or by a power source connected directly to the device or connected through a robotic surgical system.

Additional components, such as sensors or meter devices, can be directly or indirectly coupled to the motor(s) in order to determine and/or monitor at least one of displacement of a drive system or drive assembly coupled to the motor or a force on the motor during actuation of the drive system. For example, a rotary encoder can be coupled to the motor to monitor the rotational position of the motor, thereby monitoring a rotational or linear movement of a respective drive system coupled to the motor. Alternatively or in addition, a torque sensor can be coupled to the motor to determine or monitor an amount of force being applied to the motor during device operation. It is also contemplated that other ways to determine or monitor force on the motor can include (i) measuring current though the motor by using a sensor or a meter device; or (ii) measuring differences between actual velocity of the motor or components, which may include a combination of a distance travelled and an expired time, and the commanded velocity.

In certain embodiments, when the at least one motor is activated, its corresponding rotary motor shaft drives the rotation of at least one corresponding gear assembly located within the drive system of the surgical device. The corresponding gear assembly can be coupled to at least one corresponding drive shaft, thereby causing linear and/or rotational movement of the at least corresponding drive shaft. While movement of two or more drive shafts can overlap during different stages of operation of the drive system, each motor can be activated independently from each other such that movement of each corresponding drive shaft does not necessarily occur at the same time or during the same stage of operation.

When the at least one drive shaft is being driven by its corresponding motor, a rotary encoder, if used, can determine the rotational position of the motor, thereby indicating linear or rotational displacement of the at least one drive shaft. Additionally or in the alternative, when the corresponding motor is activated, the torque sensor, if used, can determine the force on the motor during linear or rotary movement of the at least one drive shaft.

Exemplary motors for use with the systems disclosed herein are described, for example, in U.S. Pat. Nos. 9,445,816 and 9,585,658 and in U.S. Patent Publication Nos. 2012/0292367, 2013/0325034, and 2015/0209059.

Anvil Clamping Drive Assembly

While the anvil clamping drive assembly 262 can have a variety of configurations, in some implementations, the anvil clamping drive assembly 262, as shown FIG. 3, can include a tube gear segment 270 that is formed on (or attached to) a proximal end 220p of the instrument shaft 218 for operable engagement with a rotational gear assembly. As shown, the rotational gear assembly can include a rotary drive gear 272 that is in meshing engaging with the tube gear segment 270. The rotational gear assembly can also include a rotation drive gear 274 that is operably coupled to a shaft motor 276.

In use, when the shaft motor 276 is activated, its corresponding rotary motor shaft drives the rotation of the rotational gear assembly, and consequently the tube gear segment 270. Activation of the shaft motor 276 can thus actuate an inner core (not shown) that extends from the tool housing 260, through the instrument shaft 220, and engages the anvil 600 at a distal end of the instrument shaft 220 such that distal advancement of the inner core can move the anvil 600 distally and proximal retraction of the inner core can move the anvil 600 proximally so that the anvil 600 can grasp tissue. Thus the inner core serves to couple with and actuate the anvil 600.

It should be noted that in some embodiments, longitudinal slots 299 of the rotary drive gear 272 of the anvil clamping drive assembly 262 can have a length that is equal to or greater than the amount of linear distance the instrument shaft 220 can move in a distal direction. As a result, the tube gear segment 270 can slide along the elongated longitudinal slots 299, during linear movement of the instrument shaft 220 without disengagement from the rotary drive gear 272. In another embodiment, the tube gear segment 270 can be engaged with longitudinal slots extending at least partially along the outer surface of the instrument shaft 220 such that the tube gear segment 270 can slide along the instrument shaft 220 when the instrument shaft 220 moves in distal and proximal directions. In such an embodiment, the rotational gear assembly can also be positioned on a longitudinal shaft that is co-linear with the instrument shaft 220 to allow the rotational gear assembly to correspondingly slide with the tube gear segment 270 so that the tube gear segment 270 and the rotational gear assembly can remain engaged. It is also contemplated that other sliding mechanisms/assemblies can be used to allow corresponding linear movement of at least the tube gear segment 270 with that of the instrument shaft 220.

Outer Staple Drive Assembly

The outer staple drive assembly 268 can have a variety of configurations. For example, as shown in FIG. 3, the outer staple drive assembly 268 can include a rotary drive gear 296 that is in meshing engagement with a rack 297A that is coupled to a drive bracket 297B having a drive shaft 297C extending therefrom and in contact with the proximal end of the outer staple driver 750. The rotary drive gear 296 can be operably coupled to a motor 298.

In use, when the motor 298 is activated by the control system 258, its corresponding rotary motor shaft drives the rotation of the rotary drive gear 296, thereby causing linear movement of the outer staple driver 750. It will be appreciated that the application of a rotary output motion from the motor 298 in one direction will result in the linear movement of the outer staple driver 750 in a distal direction to advance an outer row of staples through the distal deployment opening 222 and deploy staples into tissue (described in detail below). Further, application of the rotary output motion in an opposite direction will result in the linear movement of the outer staple driver 750 in a proximal direction to retract the outer staple driver 750 and return the outer staple driver 750 to its initial position.

Inner Staple Drive Assembly

The inner staple drive assembly 264 can have a variety of configurations. For example, as shown in FIG. 3, the inner staple drive assembly 264 can include a rotary drive gear 278 that is in meshing engagement with a rack 280 that is coupled to a drive bracket 282 having a drive shaft 284 extending therefrom and in contact with the proximal end of the inner stapler driver 770. The rotary drive gear 278 can be operably coupled to a motor 286.

In use, when the motor 286 is activated by the control system 258, its corresponding rotary motor shaft drives the rotation of the rotary drive gear 278, thereby causing linear movement of the inner stapler driver 770. It will be appreciated that the application of a rotary output motion from the motor 286 in one direction will result in the linear movement of the inner stapler driver 770 in a distal direction to advance an inner row of staples through the distal deployment opening 222 and deploy staples into tissue (described in detail below). Further, application of the rotary output motion in an opposite direction will result in the linear movement of the inner stapler driver 770 in a proximal direction to retract the inner stapler driver 770 and return the inner stapler driver 770 to its initial position.

Knife Drive Assembly

The knife drive assembly 266 can have a variety of configurations. For example, as shown in FIG. 3, the knife drive assembly 266 can include a rotary drive gear 288 that is in meshing engagement with a rack 290 that is coupled to a drive bracket 292 having a drive shaft 294 extending therefrom and in contact with the proximal end of the knife assembly 710. The rotary drive gear 288 can be operably coupled to a motor 295.

In use, when the motor 295 is activated by the control system 258, its corresponding rotary motor shaft drives the rotation of the rotary drive gear 288, thereby causing linear movement of the knife assembly 710. It will be appreciated that the application of a rotary output motion from the motor 295 in one direction will result in the linear movement of the knife assembly 710 in a distal direction to advance a knife through the distal deployment opening 222 and through tissue (described in detail below). Further, application of the rotary output motion in an opposite direction will result in the linear movement of the knife assembly 710 in a proximal direction to retract the knife assembly 710 and return the knife assembly 710 to its initial position.

End Effector

Figure 4:
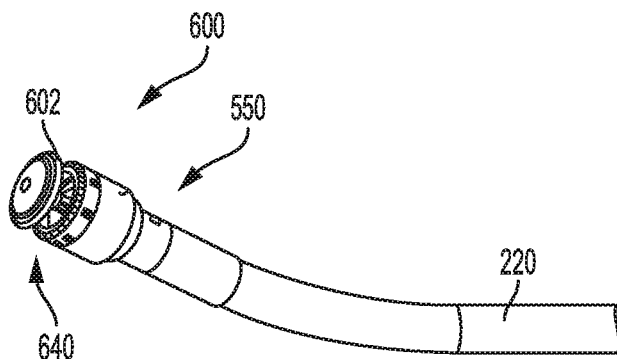
FIG. 4 is a perspective view of one embodiment of a circular staple shaft assembly that is coupled to the surgical stapling system of FIG. 3.
Figure 5:
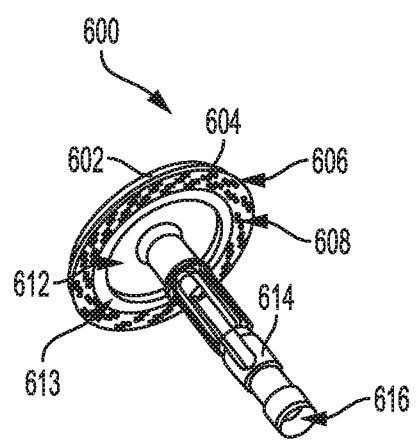
FIG. 5 is a perspective view of an anvil of the circular staple shaft assembly of FIG. 4.

As illustrated in FIG. 4, the distal end of the instrument shaft 220 can have an end effector 550 with the anvil 600, the outer staple driver 750, the inner stapler driver 770, and the knife assembly 710. As best seen in FIG. 5, the anvil 600 has a head 602 and a shank 614. The head 602 includes a proximal surface 604 that defines an outer annular array of staple forming pockets 606 and an inner annular array of staple forming pockets 608. The staple forming pockets 606, 608 are configured to deform staples 702 as staples 702 are driven into the staple forming pockets 606, 608. For instance, each stapling forming pocket 606, 608 can be configured to deform a generally "U" shaped staple 702 into a "B" shape. The proximal surface 604 terminates at an inner edge which defines an outer boundary for an annular recess 612 surrounding the shank 614. As will be described in greater detail below, the outer annular array of stapling forming pockets 606 are configured to receive staples 702 from a staple deck or cartridge 640 driven by the outer staple driver 750 while the inner annular array of staple forming pockets 608 are configured to receive staples 702 from the cartridge 640 driven by the inner staple driver 770. An inner cutting surface 613 faces proximally toward the knife assembly 710 and is configured to receive a distal-most cutting edge of the knife assembly 710 thereon to sever tissue. As discussed in more detail below, the inner cutting surface 613 can have a variety of cutting surfaces or washers formed thereon. An engagement opening 616 is formed in a proximal end of the shank 614 and configured to receive the inner core extending from the tool housing 260 and through the instrument shaft 220 to allow proximal and distal motion of the anvil 600 to grasp tissue to be stapled and severed between the anvil 600 and the cartridge 640.

Figure 6:
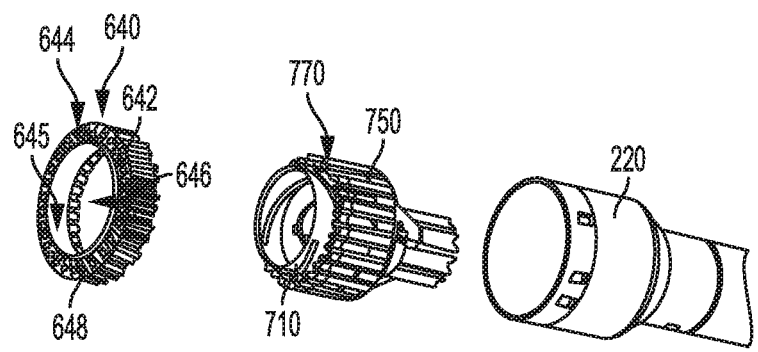
FIG. 6 is an exploded perspective view of an end effector of the circular staple shaft assembly of FIG. 4.

As illustrated in FIG. 6, the cartridge 640 is configured to be disposed on a distal end of the instrument shaft 220 and includes a tissue-facing surface 642 and a plurality of tissue grasping protrusions 648. The cartridge 640 also can have an opening 646 therethrough, an outer concentric annular array of staple openings 644, and an inner concentric annular array of stapling openings 645. A plurality of staples 702 are housed in both staple openings 644, 645. The staple openings 644, 645 are configured to align with the staple forming pockets 606, 608, respectively, when the anvil 600 and the cartridge 640 compress tissue between the proximal surface 604 and the tissue-facing surface 642. As will be described in greater detail below, the staple openings 644, 645 are configured to receive respective portions of the outer staple driver 750 and the inner staple driver 770 to drive staples from the cartridge 640 and into tissue, and the opening 646 is configured to receive the knife assembly 710 therethrough.

Figure 7:
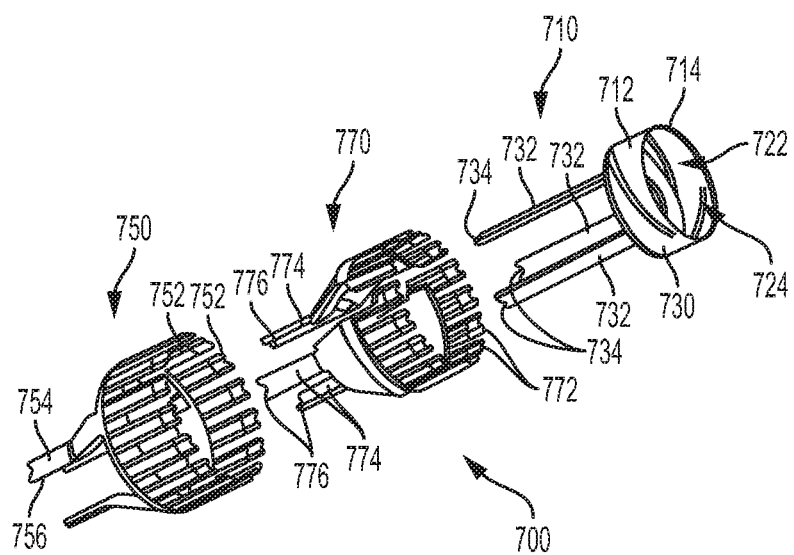
FIG. 7 is an exploded view of an outer staple driver, an inner staple driver, and a knife assembly of the circular staple shaft assembly of FIG. 4.

As best seen in FIG. 7, the outer staple driver 750 includes an annular array of staple firing members 752, three proximally presented firing legs 754 each terminating into a drive coupler 756. The outer staple driver 750 defines a bore dimensioned to slidably house the inner staple driver 770. The staple firing members 752 are each dimensioned and configured to actuate within a respective staple opening of outer concentric annular array of staple openings 644 to drive staples 702 against a respective staple forming pocket from the outer annular array of staple forming pockets 606. The proximally presented firing legs 754 and respective drive couplers 756 are configured to selectively align with and couple to a distal-most end of the drive shaft 297C such that distal linear movement of the drive shaft 297C is configured to advance the outer staple driver 750 into the cartridge 640 and fire staples therein into the anvil 600 independently of both the knife assembly 710 and the inner staple driver 770. Engagement between the firing legs 754 and respective drive couplers 756 and the distal-most end of the drive shaft 297C can occur in a variety of ways, for example firing pins 428 can be disposed on the distal-most end of the drive shaft 297C to engage the drive couplers 756 upon distal linear movement.

Figure 8:
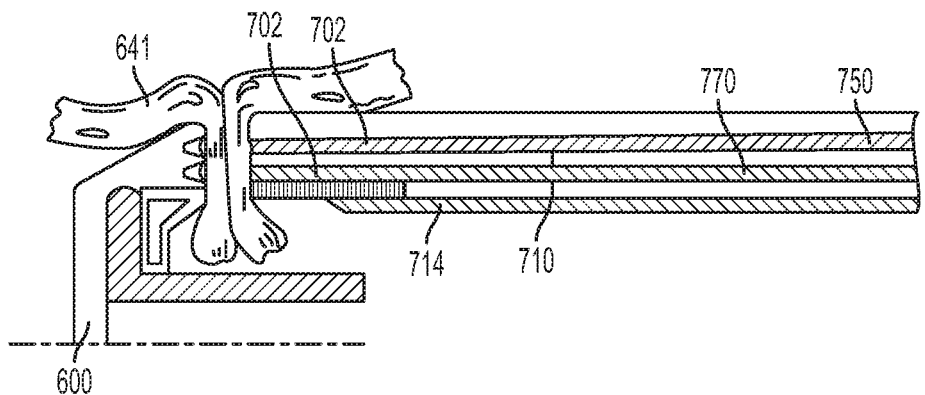
FIG. 8 is a cross-sectional side view of the circular staple shaft assembly of FIG. 4 in use.

The inner staple driver 770 includes a plurality of inner staple driver sections 780, each configured to be slidably housed between respective sectors defined by the firing legs 754 of the outer staple driver 750. The inner staple driver sections 780 define a bore dimensioned to slidably house the knife assembly 710, and each inner staple driver section 780 is located within the bore of the outer staple driver 750 such that the knife assembly 710 is nested within the inner staple driver 700, which is nested within the outer staple driver 750, as illustrated in FIG. 8. Each inner staple driver section 780 includes a plurality of staple drivers 772 dimensioned to actuate within a respective staple opening of inner concentric annular array of staple openings 645 to drive staples 702 against the inner annular array of staple forming pockets 608 in the anvil 600. Additionally, each inner staple driver section 780 includes a proximally presented firing leg 774 with a drive coupler 776. The proximally presented firing legs 774 and the respective drive couplers 776 are positioned to selectively align with and couple to a distal-most end of the drive shaft 284 such that distal linear movement of the drive shaft 284 is configured to advance the inner staple driver 770 into the cartridge 640 and fire staples therein into the anvil 600 independently of both the knife assembly 710 and the outer staple driver 750. Engagement between the firing legs 774 and the respective drive couplers 776 and the distal-most end of the drive shaft 284 can occur in a variety of ways, for example firing pins 428 can be disposed on the distal-most end of the drive shaft 284 to engage the drive couplers 756 upon distal linear movement.

The knife assembly 710 includes a cylindrical knife member 712 and a coupling ring 730. The cylindrical knife member 712 includes a distal cutting edge 714 configured to be received through opening 646 of the cartridge and configured to sever tissue against the cutting surface 613 of the anvil 600. The coupling ring 730 also includes three proximally presented firing legs 732, each terminating into a drive coupler 734. The proximally presented firing legs 732 and the respective drive couplers 734 are positioned to selectively align with and couple to a distal-most end of the drive shaft 294 such that distal linear movement of the drive shaft 294 is configured to advance the knife assembly 710 through the cartridge 640 to reach tissue to be cut against the anvil 600 independently of both the outer staple driver 750 and the inner staple driver 770. Engagement between the firing legs 732 and the respective drive couplers 734 and the distal-most end of the drive shaft 294 can occur in a variety of ways, for example firing pins 428 can be disposed on the distal-most end of the drive shaft 294 to engage the drive couplers 734 upon distal linear movement.

Stages of Operation

In use, the drive system can have one or more stages of operation. In general, the control system actuates one or more motors for driving movement/action of the drive system for each stage of operation of the drive system. That is, during each stage of operation the control system activates one or more motors to drive the corresponding one or more drive assemblies to effect a rotation and/or linear movement of particular elements of the staple shaft assembly, such as the instrument shaft, the knife, the anvil, and/or each of the inner and outer staple formers, as described below. Thus, movement of the drive system during different stages of operation is controlled by the control system and the operation of the control system will be discussed in more detail below.

Figure 9:
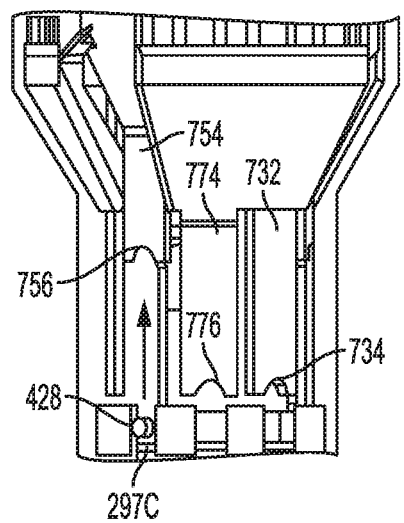
FIG. 9 is partially transparent side view of the circular staple shaft assembly of FIG. 4.

Generally, with reference to FIG. 3, actuation of one or more of the motors 298, 286, 295, 276 will cause longitudinal movement of one or more of the drive shafts 297C, 284, 294, and/or the inner core. Longitudinal movement of one or more of the drive shafts 297C, 284, 294 and/or the inner core will cause the one or more drive shafts 297C, 284, 294 and/o the inner core to engage with the corresponding outer staple driver 750, inner staple driver 770, knife assembly 710, and/or anvil 600. For example, as illustrated in FIG. 9, advancement of the drive shaft 297C will cause the firing pins 428 disposed on a distal-most end of the drive shaft 297C to engage the drive coupler 756 on the outer staple driver 750 and force the outer staple driver 750 to move distally to fire staples 702 from the cartridge 640 into tissue and against the anvil 600.

Figure 10:
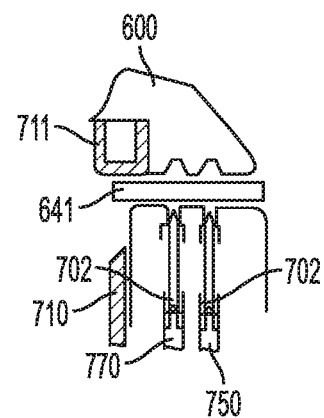
FIG. 10 is a cross-sectional side view of the circular staple shaft assembly of FIG. 4 in an initial position.
Figure 11:
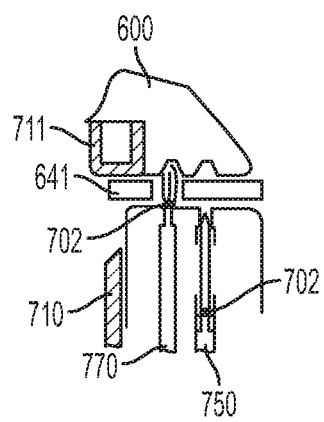
FIG. 11 is a cross-sectional side view of the circular staple shaft assembly of FIG. 10 after firing an inner row of staples.
Figure 12:
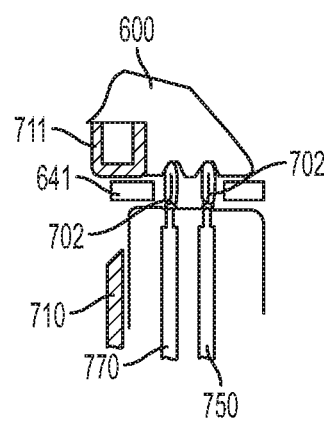
FIG. 12 is a cross-sectional side view of the circular staple shaft assembly of FIG. 11 after firing an outer row of staples.
Figure 13:
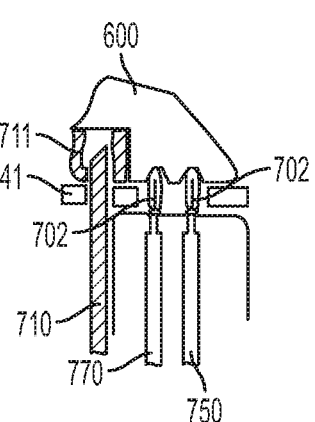
FIG. 13 is a cross-sectional side view of the circular staple shaft assembly of FIG. 12 after cutting tissue.
Figure 14:
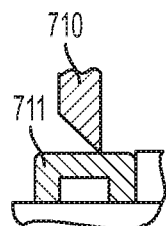
FIG. 14 is a cross-sectional side view of one embodiment of a washer for use with the circular staple shaft assembly of FIG. 4.
Figure 15:
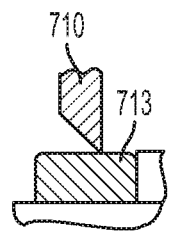
FIG. 15 is a cross-sectional side view of another embodiment of a washer for use with the circular staple shaft assembly of FIG. 4.

FIGS. 10-13 illustrate one exemplary process for stapling and cutting, however the process can occur in any order. FIG. 10 illustrates an initial configuration. FIG. 11 illustrates the inner staple driver 770 being advanced first, firing staples 702 through tissue 641 and against the anvil 600. The outer staple driver 750 is advanced next, as shown in FIG. 12, firing staples 702 against the anvil 600. Finally, as shown in FIG. 13, the knife assembly 710 is fired last to cut tissue with enough force to break a hollow washer 711. The washer 711 can represent a cutting surface, however a variety of cutting surfaces can be used. For example, FIGS. 14 and 15 illustrate a hollow washer 711 and a solid washer 713. Alternatively, a cutting surface that is part of the anvil 600 rather than having a separate washer can be used. The particular cutting surface selected for use will depend on the desired operation of the device, as will be explained below.

A rate of advancement of one or more of the outer staple driver 750, inner staple driver 770, and/or knife assembly 710 can be controlled by a variety of factors. For example, the rate can be predetermined, can be set by the control system, can be set by the user, can be based on measured tissue thickness, the type of tissue being grasped, the operation being performed, etc.

The system can control actuation and advancement of the outer staple driver 750, inner staple driver 770, and/or knife assembly 710 through a variety of different techniques. The control system can monitor a variety of different parameters to control actuation of each of the various drive assemblies. For example, the control system can monitor force, velocity, displacement, time, etc. Various exemplary techniques are discussed in more detail below.

Tissue Cutting

Figure 16:
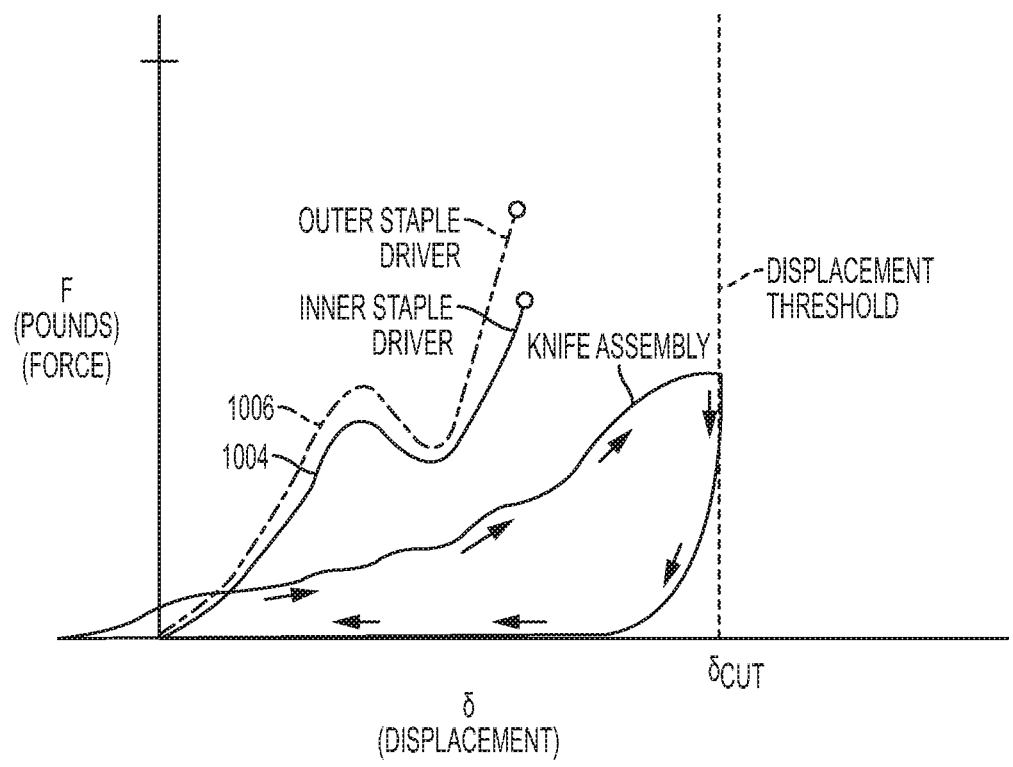
FIG. 16 is a graph illustrating the displacement of the outer staple driver, the inner staple driver, and the knife assembly of the surgical stapling system and the circular staple shaft assembly of FIGS. 2-4.

In one embodiment, the system can control actuation of the knife assembly to determine if tissue has been successfully severed. FIG. 16 illustrates a force required to displace each of the inner stapler driver, the outer staple driver, and the knife assembly during operation of the drive system. As shown, the force required to advance the inner staple driver 770 increases from an initial position to a final position. A first force peak 1004 is encountered when the inner staple driver 770 causes staples 702 to begin to deform from a pre-fired U shape to a B shape. The force will then continue to increase until the staples 702 are entirely formed to clamp tissue. The outer staple driver 750 follows a similar force trajectory, encountering an initial force peak 1006 when the staples 702 are initially formed from a pre-fired U shape to a B shape, and then continuing to increase. Advancement of both the outer and inner staple drivers 750, 770 can be controlled by controlling displacement of the drivers 750, 770. In particular, the control system can control the motors to thereby control movement of the outer and inner staple drivers 750, 770. The ultimate shape of the staples can be controlled by a variety of factors, such as the total amount of displacement of the drivers 750, 770 and the displacement of the anvil 600 (explained in detail below) relative to the staple cartridge.

As further shown in FIG. 16, the knife assembly 710 experiences a generally gradually increasing force trajectory as it is advanced to cut tissue. The system can determine when tissue has been cut by monitoring displacement of the knife assembly 710 from the tool housing 260, similar to the outer and inner staple drivers 750, 770, and it can stop and/or retract the knife assembly 710 when the knife assembly 710 reaches a predetermined displacement threshold $\delta_{CUT}$, at which point the applied force can rapidly be lowered. Displacement can be monitored through a variety of techniques, for example by using one or more rotary encoders on the motor coupled to the knife assembly 710. In such an embodiment, any cutting surface can be used in the anvil 600 because the system can determine if tissue has been cut by controlling displacement rather than by any behaviors of the cutting surface. The threshold displacement can be a pre-fixed amount or it can be altered by the system and/or a user based on the operation being performed and/or degree of tissue compression by the anvil 600.

Figure 17:
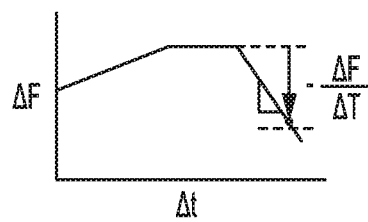
FIG. 17 is a graph illustrating a rate of change of force over time for controlling the motor force being applied to the outer staple driver, the inner staple driver, and/or the knife assembly of the surgical stapling system and the circular staple shaft assembly of FIGS. 2-4.

The control mechanism illustrated in FIG. 16 for controlling cutting is only one example, and a variety of different control mechanisms can be used to control cutting and/or staple advancement. FIG. 17 illustrates a rate of change of force over time. The system can monitor the force to advance a drive assembly coupled to one or more of the motors, for example the knife assembly 710 coupled to motor 295 for severing tissue. As the knife assembly 710 is initially advanced, the rate of change of force over time can increase, representing advancing the knife assembly 710 to encounter tissue to be cut and having a positive slope in FIG. 17. As the knife assembly 710 is forced into tissue, the rate of change of force over time can become steady, having a slope of zero. As the knife assembly 710 succeeds in cutting through tissue, the rate of change of force over time can decrease (represented by a negative slope), thus providing an indication to the system that tissue has been cut. The system can either terminate or retract the knife assembly 710 once it detects that tissue has been cut. In an exemplary embodiment, the system can look for a predetermined threshold change or delta to ensure that tissue has been entirely cut, and the threshold can be a pre-fixed amount or it can be altered by the system and/or a user based on the operation being performed and/or the degree of tissue compression by the anvil 600. If an amount of change in force of the knife assembly exceeds the predetermined threshold, the system thereby detects that tissue is fully cut and the system can terminate movement of the knife assembly or cause the knife assembly to retract. Thus when the force required to advance the knife assembly 710 changes by an amount that exceeds a predetermined threshold or delta, the control system can stop advancement of the knife assembly 710.

Figure 18:
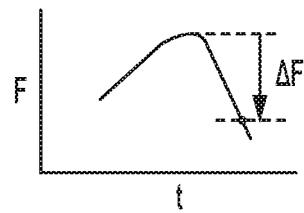
FIG. 18 is a graph illustrating a percentage drop of force over time for controlling the motor force being applied to the outer staple driver, the inner staple driver, and/or the knife assembly of the surgical stapling system and the circular staple shaft assembly of FIGS. 2-4.

In another embodiment shown in FIG. 18, the system can monitor force over time, and a predetermined force percentage drop can indicate that cutting has occurred. In particular, as the knife assembly 710 is advanced into tissue, the amount of applied force can increase and then level off as cutting is taking place. When tissue is successfully cut, however, the applied force will begin to decrease over time because there will no longer be resistance to forward movement of the knife assembly 710. If the force drops by a certain amount, the system can detect that cutting has occurred and it can stop forward advancement and/or retract the knife assembly 710. The system can thus monitor the force of the knife assembly and if the force drops by a percentage that exceeds a threshold percentage drop, this will indicate that tissue is entirely severed. As with the other thresholds, the threshold can be a pre-fixed amount or it can be altered by the system and/or a user based on the operation being performed and/or the degree of tissue compression by the anvil 600.

Figure 19:
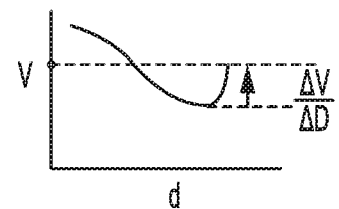
FIG. 19 is a graph illustrating change in velocity as a function of distance for controlling the motor force being applied to the outer staple driver, the inner staple driver, and/or the knife assembly of the surgical stapling system and the circular staple shaft assembly of FIGS. 2-4.

FIG. 19 illustrates another embodiment of a control mechanism that monitors velocity as a function of distance. Initially, the velocity of the knife assembly 710 can gradually decrease as the knife assembly 710 is advanced into tissue and begins to cut, since the tissue will cause the knife assembly 710 to slow down. When the tissue is fully cut, however, there can be a sudden increase in velocity, indicating that there is no longer tissue constraining the knife assembly 710. This positive increase can function to indicate to the system that tissue is fully cut, and thus the system can stop forward advancement and/or retract the knife assembly 710. The system can thereby monitor the velocity during knife advancement, and if the velocity changes by an amount that exceeds a threshold or delta increase in velocity, this will indicate that the tissue is entirely severed. As with the other thresholds, the threshold can be a pre-fixed amount or can be altered by the system and/or a user based on the operation being performed and/or the degree of tissue compression by the anvil 600. Thus when the velocity of the knife assembly 710 changes by an amount that exceeds a predetermined threshold or delta, the control system can stop advancement of the knife assembly 710.

Figure 20:
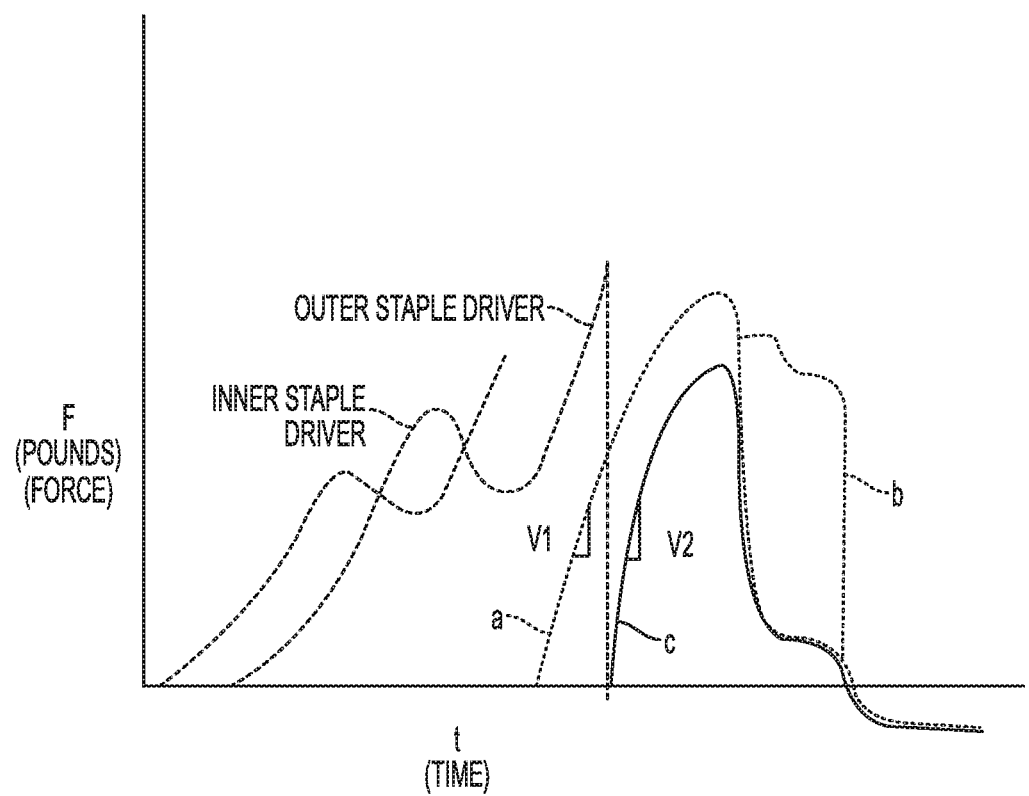
FIG. 20 is a graph illustrating force being applied over time to the outer staple driver, the inner staple driver, and the knife assembly during use of the surgical stapling system and the circular staple shaft assembly of FIGS. 2-4.

In other aspects, the control system can monitor force applied to the inner staple driver, the outer staple driver, and/or the knife assembly to determine when to cut tissue by advancing the knife assembly and when tissue has been successfully cut and the knife assembly can be safely retracted. Similar to FIG. 16, FIG. 20 illustrates force as a function of time as applied to the outer staple driver 750, the inner staple driver 770, and the knife assembly 710. As illustrated in FIG. 20, the system can determine when the knife assembly 710 is fully advanced and the tissue is fully cut by monitoring the force being applied to the knife assembly 710. The control system can monitor force on the knife assembly 710 over a variety of conditions, such as when using the hollow washer 711, when using the solid washer 713, and when firing the knife assembly 710 at different velocities. FIG. 20 illustrates the monitored force on the knife assembly 710 when using the hollow washer 711 at a first velocity $V_1$ shown by dotted line a, illustrates the monitored force on the knife assembly 710 when using the solid washer 713 at the first velocity $V_1$ shown by dotted line b, and illustrates the monitored force on the knife assembly 710 when using the hollow washer 711 at a second velocity $V_2$ shown by the solid line c. The control system can determine when to fire the knife assembly 710 by monitoring force on the inner staple driver 770 and/or the outer staple driver 750. For example, similar to the force in FIG. 16, the force required to advance the inner staple driver 770 and the outer staple driver 750 can increase from initial positions, through first force peaks, and then continue to increase until staples are entirely formed. Before staples are entirely formed, the system can begin advancement of the knife assembly 710, as illustrated in the dotted lines a, b. The system can also wait until staple formation is complete to begin advancing the knife assembly 710, as illustrated by the solid line c. The control system can monitor the force on the knife assembly 710, which will steadily increase over time as the knife assembly 710 is advanced through tissue and encounters a washer. When the knife assembly 710 encounters a washer, such as the hollow washer 711 or the solid washer 713, the control system will observe a force peak, as can be seen by the solid line c and the dotted lines a, b. The system can determine when tissue is entirely cut by detecting an initial decrease in the monitored force. For example, when the knife assembly 710 breaks through the hollow washer 711, the force on the knife assembly 710 will decrease immediately, as can be seen by the solid line c and the dotted line a. When the knife assembly 710 cuts through tissue and encounters the solid washer, the force can experience a stepped-down decrease. The control system can thus detect that tissue is entirely cut by monitoring force on the knife assembly 710. When the knife assembly 710 is fired at a faster velocity $V_2$ in comparison to velocity $V_1$, the knife assembly 710 is able to cut through tissue and break the washer 711 with less force, as can be seen in the lower force curve of the solid line c of FIG. 20 when compared to the dotted lines a, b. The greater impulse impact from the higher velocity means that less force is required to break through tissue and the washer 711.

Figure 21:
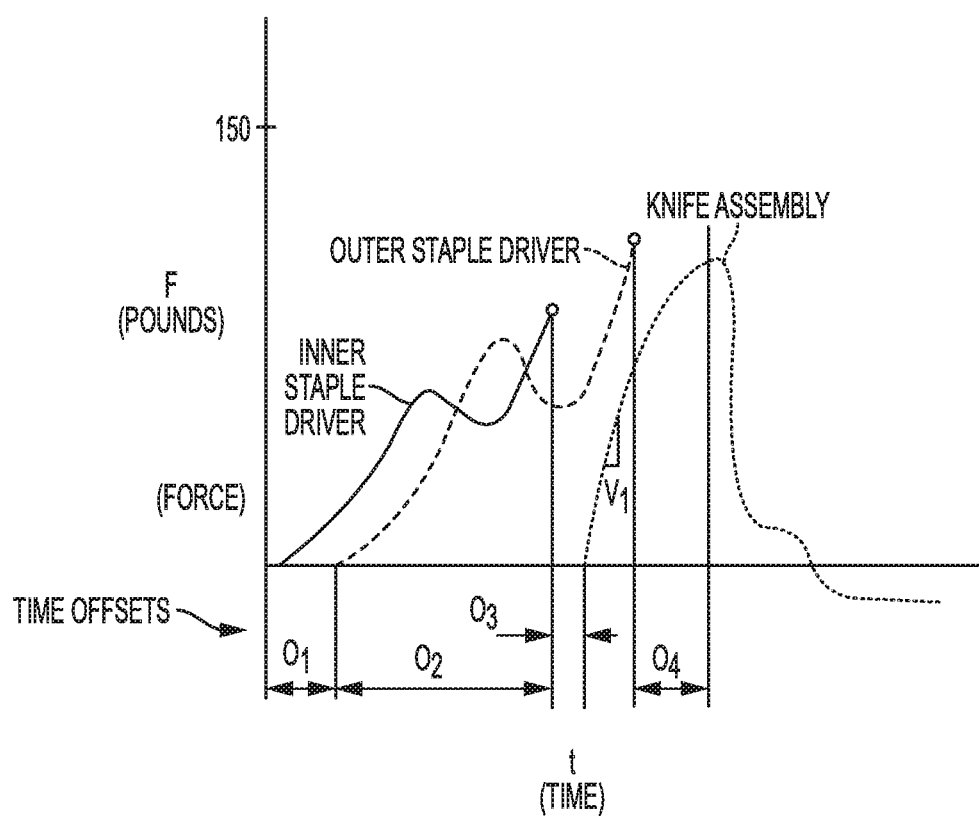
FIG. 21 is a graph illustrating force being applied over various time offsets to the outer staple driver, the inner staple driver, and the knife assembly during use of the surgical stapling system and the circular staple shaft assembly of FIGS. 2-4.

The control system can also control firing of the different drive assemblies based on timing. The control system can have predetermined time offsets that it uses to determine when to begin advancing the inner staple driver 770, the outer staple driver 750, and the knife assembly 710 based on predetermined time offsets from previous steps. FIG. 21 illustrates a graph showing force as a function of time as applied to the outer staple driver 750, the inner staple driver 770, and the knife assembly 710. In FIG. 21, the control system advances the inner staple driver 770 first, and the control system advances the outer staple driver 750 after a first offset $O_1$ of time from the advancement of the inner staple driver 770. The control system can determine when the staples of the inner circular row are completely formed by the inner staple driver 770 by waiting a second offset $O_2$ of time from advancement of the outer staple driver 750. The control system can wait a third offset $O_3$ of time from the completed formation of the inner staples, at which point the control system can begin advancing the knife assembly 710. While the knife assembly 710 is being advanced, formation of staples in the outer row of staples is completed by the outer staple driver 750. The control system can then determine when tissue has been completely cut and the knife assembly 710 should be retracted by waiting a fourth offset $O_4$ of time from when the outer staples are formed, represented by the peak of the force curve of the knife assembly 710 ($V_1$ represents the velocity of the knife assembly 710). The control system can thus use various timing offsets to control advancement of one or more of the inner staple driver 770, the outer staple driver 750, and/or the knife assembly 710 based on various previous steps in the stapling and cutting process. The offsets can be predetermined or can be changed by the system and/or the user.

Anvil Closing

Figure 22:
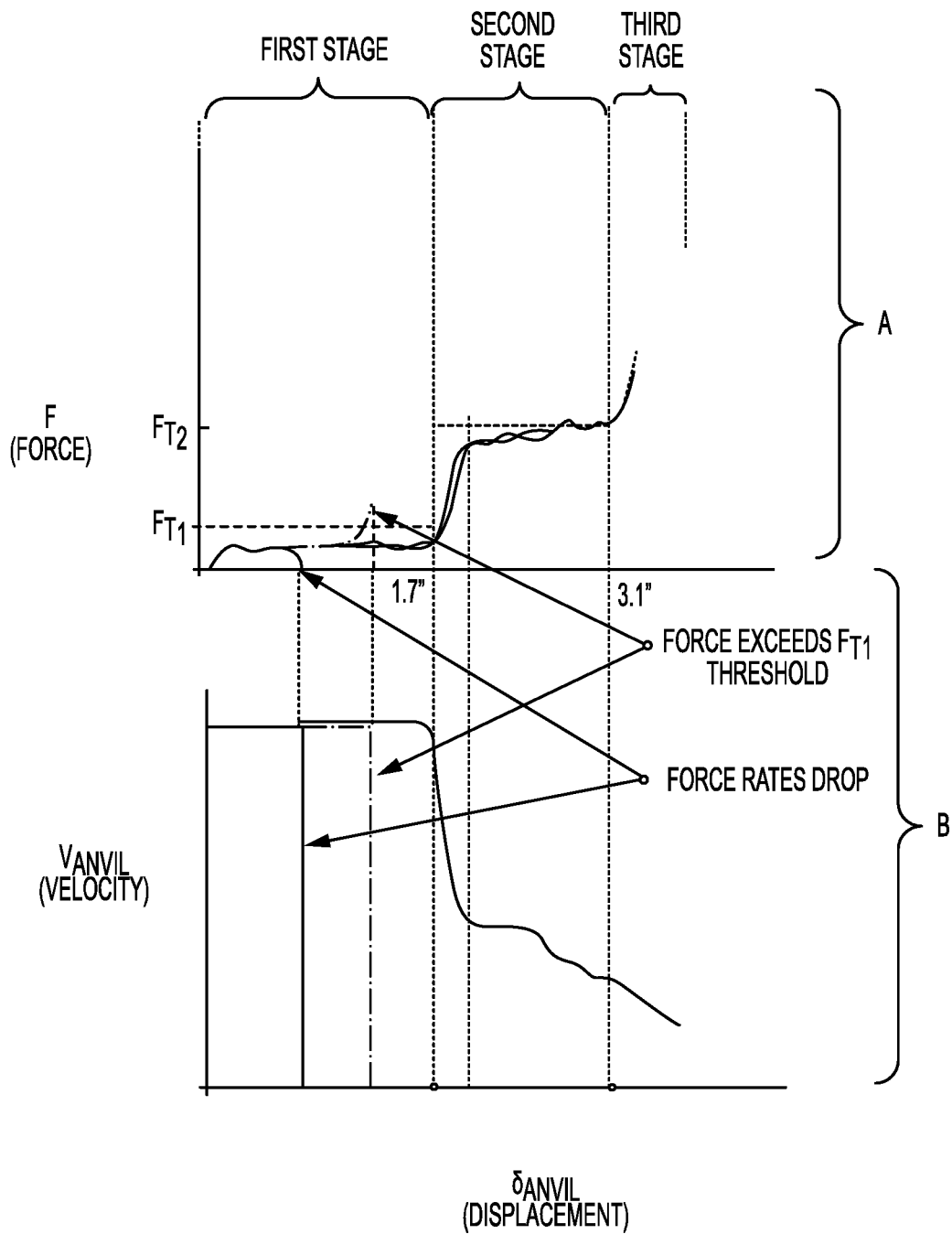
FIG. 22 is a graph illustrating force being applied and the velocity of the anvil over displacement during use of the surgical stapling system and the circular staple shaft assembly of FIGS. 2-4.

In other aspects, the control system can monitor the force and velocity on an anvil and use that information to control actuation of each drive assembly. FIG. 22 illustrates three stages of operation of the drive system 257, and in particular section A of FIG. 22 illustrates force applied to tissue as a function of displacement of the anvil, for example anvil 600, during each stage of operation. Section B of FIG. 22 illustrates velocity of the anvil as a function of displacement.

Figure 23:
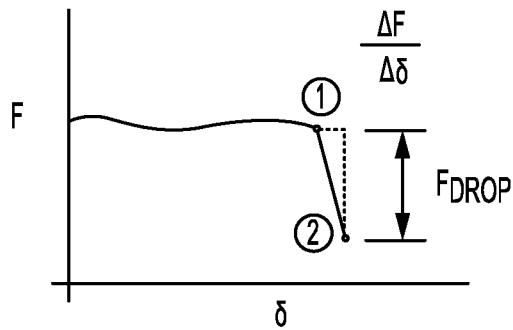
FIG. 23 is a graph illustrating the rate of change of the force being applied to the anvil over displacement during use of the surgical stapling system and the circular staple shaft assembly of FIGS. 2-4.

During the first stage, the control system can monitor the force or velocity during closing of the anvil 600 to detect if an error has occurred. In the first stage, the anvil 600 experiences a quick close operation to rapidly grasp tissue, for example by grasping tissue between the anvil 600 and the cartridge 640. While the circular stapler anvil 600 and the cartridge 640 will be discussed herein, the three stages of operation of the drive system can be applied to any tissue-clamping device. During stage one, the anvil 600 is rapidly closed and is therefore displaced by a first distance, e.g., approximately 1.7 inches in the illustrated embodiment. However, there are at least two situations where the drive system can determine that a malfunction has occurred. If an error has occurred, such as an obstruction preventing proper closure of the anvil 600, the force will spike, as shown in section A. If the force being applied to the anvil 600 exceeds a predetermined threshold $F_{T1}$ during displacement of the anvil in the first stage, the system can determine that an error has occurred and the system can stop the clamping action of the anvil 600. As shown in section B, if an error has occurred, the velocity of the anvil 600 will rapidly decline during the first stage. The system can thus monitor force and/or velocity changes to detect if an error has occurred. Alternatively, if the force being applied declines suddenly, the system can likewise determine that an error has occurred, such as the anvil 600 becoming loose from the device. This is shown in FIG. 23. If the force drops by an amount that exceeds a predetermined threshold rate $F_{drop}$ (from a force at point 1 to a force at point 2 in FIG. 23), the system can determine that the anvil 600 might have popped off of the device. The system can stop the clamping action of the anvil 600 and/or reverse the clamping process. As shown in section A of FIG. 22, this is represented by a rapid decline in the force curve. As shown in section B, this can also be represented by a rapid decline in the velocity of the anvil 600.

During the second stage, tissue continues to be compressed by the anvil 600. The anvil 600 approaches an optimal compression level of the tissue during this stage, as can be seen by the force curve in section A approaching the threshold $F_{T2}$, representing the optimum compression. The system can monitor the force to move the anvil, and once the force exceeds the threshold $F_{T2}$, the system can allow staples to be fired. Also during this stage, as illustrated in section B, the velocity of the anvil will slow down to allow for a better compression of tissue grasped during the quick close of the first stage. In an exemplary embodiment, optimum compression can occur at an anvil displacement of at least approximately 3.1 inches.

During the third stage, staple formation occurs. Force on the anvil 600 can increase as the staples are fully formed, and the velocity of the anvil can decline and/or stop entirely once the optimum compression is reached, as selected by the user, and the tissue does not need further clamping.

Because the control system can monitor and determine the displacement of the anvil 600, the control system can determine a gap size between the anvil 600 and the cartridge 640. The control system can use this information to determine a thickness of the tissue grasped by the anvil 600. The control system can alter the distance that the inner staple drive assembly 770, the outer staple drive assembly 750, and the knife assembly 710 are advanced based on the gap size or thickness of the tissue between the anvil 600 and the cartridge 640. For example, the inner staple drive assembly 770, the outer staple drive assembly 750, and/or the knife assembly 710 can be advanced farther when the system determines that the grasped tissue is thick. The control system can also alter the rates of advancement of one or more of the inner staple drive assembly 770, the outer staple drive assembly 750, and the knife assembly 710 based on the thickness of the tissue engaged between the anvil 600 and the cartridge 640. As the tissue thickness increases, the system can reduce the rates of advancement of one or more of the inner staple drive assembly 770, the outer staple drive assembly 750, and the knife assembly 710 to compensate for the thicker tissue.

Staple Formation

Figure 24:
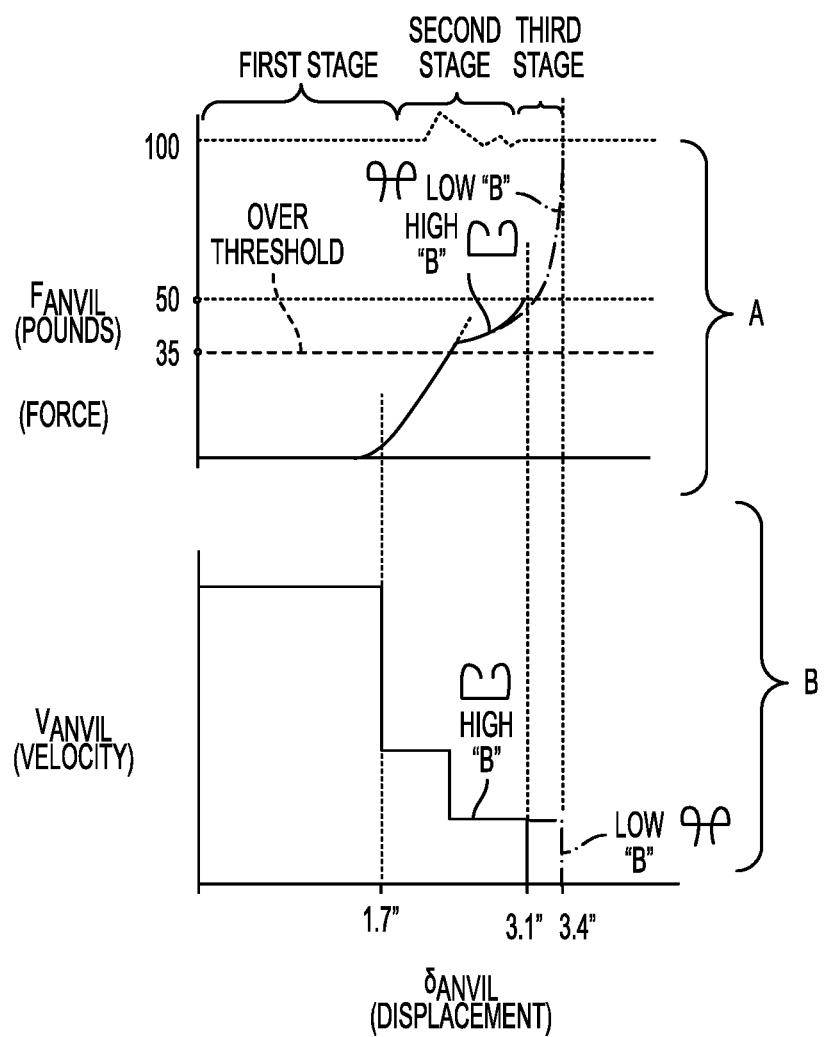
FIG. 24 is a graph illustrating force being applied and the velocity of the anvil over displacement during use of the surgical stapling system and the circular staple shaft assembly of FIGS. 2-4.

The control system can also monitor and control the position of the anvil to form the staple to a desired shape, such as a high "B" or a low "B". FIG. 24 illustrates three stages of operation of the drive system during anvil displacement to control staple formation, and in particular section A of FIG. 24 illustrates force applied to tissue as a function of displacement of the anvil 600 to clamp tissue during each stage of operation. Section B of FIG. 24 illustrates a velocity of the anvil as a function of displacement. The control system can control the velocity of the anvil 600 based on the displacement of the anvil 600 in order to achieve the desired compression of clamped tissue. During the first stage, which is a quick close stage as in FIG. 22, the control system can monitor the force on and the displacement of the anvil 600, and the control system can control the velocity of the anvil 600 as it is rapidly displaced. The force begins to rise as the anvil approaches approximately a first distance, e.g., 1.7 inches of displacement in the illustrated embodiment. An initial increase in the force will indicate to the system that the anvil 600 has made contact with tissue, as illustrated in section A. Section B illustrates the rapid but constant velocity of the anvil 600 as the anvil closes on tissue. During the second stage, the tissue continues to be compressed by the anvil 600. The force will exceed an overload threshold value, thereby causing the control system to focus on load control of the force being applied to the tissue to reach an optimum compression. The velocity of the anvil during this stage experiences a stepped-down decline as the quick close stage ends and the slower tissue clamping occurs. At the end of the second stage, the displacement of the anvil 600 approaches approximately 3.1 inches, in the illustrated embodiment. When displacement of the anvil is at approximately 3.1 inches, the system can allow firing of staples to form High "B" staples, as illustrated on the graph in FIG. 24. High "B" staples are staples in which the legs of the staple have begun to curl back toward the base of the staple but have not reached the base of the staple. High "B" staples can be used when a user or the system desires less compression and therefore a less-compressed staple. If a user and/or the system desire this level of compression, displacement of the anvil 600 can be stopped at this point and the force can remain constant while the velocity falls to zero. However, compression can be increased up to 3.4 inches of displacement, at which point the staples will be formed into Low "B" staples, as illustrated on the graph in FIG. 24. Low "B" staples are staples in which the legs of the staple are curled back toward the base of the staple and cross over the base of the staple to form a very compressed staple. Low "B" staples can be used when a user or the system desires a greater level of compression and thus a more compressed staple relative to the High "B" staples. If a user and/or the system desire this level of compression, displacement of the anvil 600 can be continued until the desired level of compression is reached, causing the force to increase and the velocity to continue at a constant level until the desired compression is reached. A preferred compression zone can be between approximately 3.1 inches of displacement and 3.4 inches of displacement, and the compression level can be predetermined, set by the system, and/or set by the user depending on the operation to be performed and tissue to be grasped. Accordingly, the system can control staple formation by controlling the velocity of the anvil to achieve a desired displacement of the anvil.

For each stage of operation there can be at least one predetermined motor force threshold and/or a displacement threshold determined by current monitor(s), rotary encoder(s), etc. (as discussed above).

Operation of Control System

Generally, as discussed above, the control system can control movement and actuation of a surgical device. For example, the control system can include at least one computer system and can be operably coupled to the at least one motor that drives a drive system on the surgical device. The computer system can include components, such as a processor, that are configured for running one or more logic functions, such as with respect to a program stored in a memory coupled to the processor. For example, the processor can be coupled to one or more wireless or wired user input devices ("UIDs"), and it can be configured for receiving sensed information, aggregating it, and computing outputs based at least in part on the sensed information. These outputs can be transmitted to the drive system of surgical device to control the surgical device during use.

In certain embodiments, the control system can be a closed-loop feedback system. The stored data within the computer system can include predetermined threshold(s) for one or more stages of operation of the drive system. When the control system is actuated, it drives one or more motors on or coupled to the surgical device, consequently actuating the drive system through each stage of operation. During each stage of operation, the control system can receive feedback input from one or more sensors coupled to the motor(s) that sense displacement and/or torque of the motor(s). The computer system can aggregate the received feedback input(s), perform any necessary calculations, compare it to the predetermined threshold for the corresponding stage of operation, and provide output data to the motor(s). If at any time during each stage of operation the control system determines that the received input exceeds a maximum predetermined threshold or is less than a minimum predetermined threshold, the control system can modify the output data sent to the motor based on the programmed logic functions. For example, the control system can modify the output data sent to the motor(s) to reduce a current delivered to the motor to reduce motor force or a voltage delivered to the motor to thereby reduce a rotational speed of the motor(s) or to stop movement of the motor(s).

Referring back to FIGS. 2 and 3, the control system 258, which includes at least one computer system, can be operably coupled (wired or wirelessly) to each of the motors 276, 286, 295, 298 that drive the various components of the drive system 257. As described above, for each stage of operation one or more motors 276, 286, 295, 298 are actuated by the control system 258. As a result, the control system 258 can control the movement of at least one of the instrument shaft 220, the pusher 234, the anvil 228, and the staple former 226. In particular, the control system 258 can monitor a force required to move each of the outer staple driver, the inner staple driver, the anvil, and the knife assembly during each stage of operation, can compare the monitored force to various threshold forces, and can modify or terminate current applied to the motor to thereby modify or terminate movement of the anvil, staple drivers, and/or knife assembly.

In other embodiments, mechanical stops can be used to control displacement of the staple drivers, anvil, and/or the knife assembly during each stage of operation. That is, rather programming the computer system with displacement data, as described above, one or more mechanical stops can be used to control displacement during each stage of operation. Thus, the control system can modify the output data sent to the motors to cease movement (or in the alternative, reduce current to the motor to reduce motor speed) when a mechanical stop is engaged (as would be indicated by a force spike) or the force applied by a motor exceeds a predetermined threshold.

In other embodiments, for each stage of operation, the control system can control the force applied by each motor based on predetermined motor force thresholds and can monitor the displacement once these thresholds have been met. That is, during each stage of operation, when the control system determines that the predetermined motor force(s) have been met, the control system can then measure the displacement to determine the position of the staple drivers, anvil, and/or knife assembly.

As discussed above, the control system disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 25:
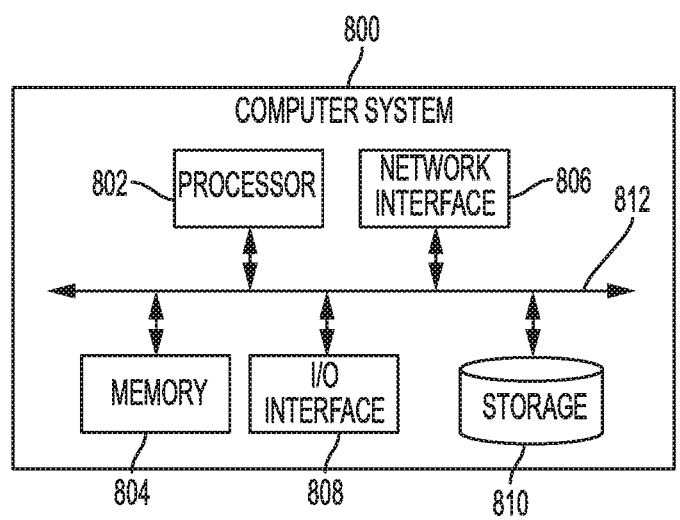
FIG. 25 illustrates one exemplary embodiment of a computer system that can be used to implement a control system of the present disclosure.

FIG. 25 illustrates one exemplary embodiment of a computer system 800. As shown, the computer system 800 includes one or more processors 802 which can control the operation of the computer system 800. "Processors" are also referred to herein as "controllers." The processor(s) 802 can include any type of microprocessor or central processing unit (CPU), including programmable general-purpose or special-purpose microprocessors and/or any one of a variety of proprietary or commercially available single or multi-processor systems. The computer system 800 can also include one or more memories 804, which can provide temporary storage for code to be executed by the processor(s) 802 or for data acquired from one or more users, storage devices, and/or databases. The memory 804 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 800 can be coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 can also include one or more network interface(s) 806, one or more input/output (IO) interface(s)

808 that can include one or more interface components, and one or more storage device(s) 810.

The network interface(s) 806 can enable the computer system 800 to communicate with remote devices, e.g., motor(s) coupled to the drive system 257 that is located within the surgical device or a robotic surgical system or other computer systems, over a network, and can be, for non-limiting example, remote desktop connection interfaces, Ethernet adapters, and/or other local area network (LAN) adapters. The IO interface(s) 808 can include one or more interface components to connect the computer system 800 with other electronic equipment, such as the sensors located on the motor(s). For non-limiting example, the IO interface(s) 808 can include high speed data ports, such as universal serial bus (USB) ports, 1394 ports, Wi-Fi, Bluetooth, etc. Additionally, the computer system 800 can be accessible to a human user, and thus the IO interface(s) 808 can include displays, speakers, keyboards, pointing devices, and/or various other video, audio, or alphanumeric interfaces. The storage device(s) 810 can include any conventional medium for storing data in a non-volatile and/or non-transient manner. The storage device(s) 810 can thus hold data and/or instructions in a persistent state, i.e., the value(s) are retained despite interruption of power to the computer system 800. The storage device(s) 810 can include one or more hard disk drives, flash drives, USB drives, optical drives, various media cards, diskettes, compact discs, and/or any combination thereof and can be directly connected to the computer system 800 or remotely connected thereto, such as over a network. In an exemplary embodiment, the storage device(s) 810 can include a tangible or non-transitory computer readable medium configured to store data, e.g., a hard disk drive, a flash drive, a USB drive, an optical drive, a media card, a diskette, a compact disc, etc.

The elements illustrated in FIG. 25 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

In an exemplary embodiment, the computer system 800 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical stapling system, comprising:
a circular stapling tool having a housing and an instrument shaft extending therefrom with an end effector at a distal end thereof, the end effector including a staple deck and an anvil movable relative to the staple deck, the circular stapling tool being configured to drive inner and outer circular rows of staples through tissue engaged between the staple deck and the anvil to thereby staple the tissue, and being configured to drive a knife through tissue engaged between the staple deck and the anvil to thereby cut the tissue; and
a control system configured to communicate with the circular stapling tool and configured to selectively actuate the circular stapling tool to selectively drive only one of the inner circular row of staples, the outer circular row of staples, and the knife while the other two of the inner circular row of staples, the outer circular row of staples, and the knife remain stationary.

2. The surgical stapling system of claim 1, wherein the control system is configured to initiate actuation of the knife prior to commencement of actuation of at least one of the inner circular row of staples and the outer circular row of staples.

3. The surgical system of claim 1, wherein the housing comprises a tool mounting portion configured to mount to a motor housing on a surgical robot.

4. The surgical system of claim 1, wherein the control system is configured to control a displacement of the anvil from the staple deck and drive the knife when a threshold displacement is reached.

5. The surgical system of claim 1, wherein the control system is configured to monitor a displacement of the knife from the housing and retract the knife when the knife reaches a threshold displacement away from the housing.

6. The surgical system of claim 1, wherein the control system is configured to drive any one of the inner circular row of staples, the outer circular row of staples, and the knife based on a predetermined time offset after driving one of the others of the inner circular row of staples, the outer circular row of staples, and the knife.

7. The surgical stapling system of claim 1, wherein the circular stapling tool includes an inner staple drive assembly operable to drive the inner circular row of staples through the staple deck toward the anvil, an outer staple drive assembly operable to drive the outer circular row of staples through the staple deck toward the anvil, and a knife drive assembly configured to drive the knife through the staple deck toward the anvil; and
wherein each of the inner staple drive assembly, the outer staple drive assembly, and the knife drive assembly is configured to be actuated without actuating the others of the inner staple drive assembly, the outer staple drive assembly, and the knife drive assembly.

8. The surgical system of claim 7, wherein the control system is configured to control a travel distance of the inner staple drive assembly and the outer staple drive assembly.

9. The surgical system of claim 7, wherein the control system is configured to control a rate of advancement of at least one of the inner staple drive assembly, the outer staple drive assembly, and the knife drive assembly based on a measured thickness of a tissue engaged between the anvil and the staple deck.

10. The surgical system of claim 7, wherein the inner staple drive assembly comprises a first rotary drive gear in meshing engagement with a first rack, the first rack is coupled to a first drive bracket having a first drive shaft extending therefrom, and the first drive shaft is in contact with an inner stapler driver configured to drive the inner circular row of staples;
wherein the outer staple drive assembly comprises a second rotary drive gear in meshing engagement with a second rack, the second rack is coupled to a second drive bracket having a second drive shaft extending therefrom, and the second drive shaft is in contact with an outer staple driver configured to drive the outer circular row of staples; and
wherein the knife drive assembly comprises a third rotary drive gear in meshing engagement with a third rack, the third rack is coupled to a third drive bracket having a third drive shaft extending therefrom, and the third drive shaft is in contact with a proximal end of the knife and configured to drive the knife.

11. The surgical system of claim 1, further comprising first, second, and third motors, wherein the first motor is configured to drive the inner circular row of staples, the second motor is configured to drive the outer circular row of staples, and the third motor is configured to drive the knife, and wherein the first, second, and third motors are configured to be selectively actuated such that only one of the first, second, and third motors is actuated at once.

12. A surgical stapling system, comprising:
an electromechanical tool including an instrument shaft and an end effector at a distal end thereof, the end effector including
a staple deck having inner and outer rows of staples disposed therein,
an anvil movable relative to the staple deck,
an inner staple driver operable to drive the inner row of staples through the staple deck toward the anvil,
an outer staple driver operable to drive the outer row of staples through the staple deck toward the anvil,
a knife forming a complete circle and movable through an opening in the staple deck for cutting tissue engaged between the staple deck and the anvil;
a housing coupled to the shaft, the housing having drive assemblies comprising
an inner staple drive assembly operable to drive the inner stapler driver,
an outer staple drive assembly operable to drive the outer staple driver,
a knife drive assembly operable to drive the knife; and
a control system configured to communicate with the electromechanical tool and configured to selectively drive only one of the inner staple drive assembly, the outer staple drive assembly, and the knife drive assembly while the other two of the inner staple drive assembly, the outer staple drive assembly, and the knife drive assembly remain stationary.

13. The surgical system of claim 12, wherein the control system is configured to control a travel distance of the inner staple drive assembly and the outer staple drive assembly to thereby control a shape of staples being formed by the anvil.

14. The surgical system of claim 12, wherein the control system is configured to control a rate of advancement of at least one of the inner staple drive assembly, the outer staple drive assembly, and the knife drive assembly based on a measured thickness of a tissue engaged between the anvil and the staple deck.

15. The surgical system of claim 12, wherein the housing comprises a tool mounting portion configured to mount to a motor housing on a surgical robot.

16. The surgical system of claim 12, wherein the outer staple drive assembly is configured to cause the outer staple driver to advance in distal and proximal directions relative to the housing to deploy staples upon actuation, the inner staple drive assembly is configured to cause the inner stapler driver to advance in distal and proximal directions relative to the housing to deploy staples upon actuation, and the knife drive assembly is configured to cause the knife to advance in distal and proximal directions relative to the housing to sever tissue upon actuation.

17. The surgical system of claim 16, further comprising first, second, and third motors, the first motor being in operational engagement with the outer staple drive assembly, the second motor being in operational engagement with the inner staple drive assembly, and the third motor being in operational engagement with the knife drive assembly.

18. The surgical system of claim 12, wherein the knife drive assembly comprises a rotary drive gear in meshing engagement with a rack, the rack is coupled to a drive bracket having a drive shaft extending therefrom, the drive shaft is in contact with a proximal end of the knife, and the rotary drive gear is configured to rotate to cause linear distal and proximal movement of the knife.

19. The surgical system of claim 12, wherein the outer staple drive assembly comprises a rotary drive gear in meshing engagement with a rack, the rack is coupled to a drive bracket having a drive shaft extending therefrom, the drive shaft is in contact with a proximal end of the outer staple driver, and the rotary drive gear is configured to rotate to cause linear distal and proximal movement of the outer staple driver.

20. The surgical system of claim 12, wherein the inner staple drive assembly comprises a rotary drive gear in meshing engagement with a rack, the rack is coupled to a drive bracket having a drive shaft extending therefrom, the drive shaft is in contact with a proximal end of the inner stapler driver; and the rotary drive gear is configured to rotate to cause linear distal and proximal movement of the inner stapler driver.

* * * * *